US010420881B2

(12) United States Patent
Sonderegger et al.

(10) Patent No.: US 10,420,881 B2
(45) Date of Patent: Sep. 24, 2019

(54) SELF-INJECTION DEVICE

(71) Applicant: Becton, Dickinson and Company, Franklin Lakes, NJ (US)

(72) Inventors: Ralph Sonderegger, Farmington, UT (US); Lionel Vedrine, Palo Alto, CA (US); Curt Bingham, Hyde Park, UT (US); Bart Peterson, Farmington, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 140 days.

(21) Appl. No.: 15/604,477

(22) Filed: May 24, 2017

(65) Prior Publication Data

US 2017/0252510 A1 Sep. 7, 2017

Related U.S. Application Data

(63) Continuation of application No. 14/606,935, filed on Jan. 27, 2015, now Pat. No. 9,919,097, which is a (Continued)

(51) Int. Cl.
*A61M 5/142* (2006.01)
*A61M 5/32* (2006.01)
(Continued)

(52) U.S. Cl.
CPC .... *A61M 5/14248* (2013.01); *A61M 5/14244* (2013.01); *A61M 5/1626* (2013.01);
(Continued)

(58) Field of Classification Search
CPC .......... A61M 5/14248; A61M 5/14252; A61M 5/3202
See application file for complete search history.

(56) References Cited

U.S. PATENT DOCUMENTS 1,779,451 A 10/1930 Sponsel
3,048,171 A 8/1962 Grau
(Continued)

FOREIGN PATENT DOCUMENTS

CN 1671430 A 9/2005
CN 101346157 1/2009
(Continued)

*Primary Examiner* — Laura A Bouchelle
(74) *Attorney, Agent, or Firm* — Dickinson Wright PLLC

(57) ABSTRACT

A drug delivery device (100), including a body (104, 116) having a reservoir (164, 176) disposed therein for containing a medicament and an injection needle (152) for penetrating the skin of a patient, the needle (152) providing a path for the medicament between the reservoir (164, 176) and the patient. The device (100) also includes a needle cover (114) for selectively covering the injection needle (152), an adhesive (264) for selectively adhering the device to the patient, a release liner (500) for selectively covering a patient side of the adhesive (264), and a connecting means (112, 520, 512, 508, 524) for connecting the needle cover (114) and the release liner (500) such that removal of one of the needle cover (114) and the release liner (500) from the device (100) removes the other one of the needle cover (114) and the release liner (500).

11 Claims, 22 Drawing Sheets

Related U.S. Application Data continuation of application No. 13/516,540, filed as application No. PCT/US2009/006573 on Dec. 16, 2009, now Pat. No. 8,961,469.

(51) Int. Cl.
*A61M 5/162* (2006.01)
*A61M 5/14* (2006.01)

(52) U.S. Cl.
CPC ........ *A61M 5/3202* (2013.01); *A61M 5/3213* (2013.01); *A61M 2005/1416* (2013.01)

(56) References Cited

U.S. PATENT DOCUMENTS

| | | |
|---|---|---|
| 3,814,097 A | 6/1974 | Ganderton et al. |
| 3,964,482 A | 6/1976 | Gerstel et al. |
| 4,196,732 A | 4/1980 | Wardlaw |
| 4,258,711 A | 3/1981 | Tucker et al. |
| 4,316,463 A | 2/1982 | Schmitz et al. |
| 4,340,048 A | 7/1982 | Eckenhoff |
| 4,424,911 A | 1/1984 | Resnick |
| 4,498,843 A | 2/1985 | Schneider et al. |
| 4,525,164 A | 6/1985 | Loeb et al. |
| 4,552,561 A | 11/1985 | Eckenhoff et al. |
| 4,610,672 A | 9/1986 | Ewalt et al. |
| 4,634,427 A | 1/1987 | Hannula et al. |
| 4,664,654 A | 5/1987 | Strauss |
| 4,772,263 A | 9/1988 | Dorman et al. |
| 4,781,688 A | 11/1988 | Thoma et al. |
| 4,886,499 A | 12/1989 | Cirelli et al. |
| 4,921,475 A | 5/1990 | Sibalis |
| 4,998,918 A | 3/1991 | Mimura |
| 5,011,477 A | 4/1991 | Winchell et al. |
| 5,045,064 A | 9/1991 | Idriss |
| 5,090,963 A | 2/1992 | Gross et al. |
| 5,137,516 A | 8/1992 | Rand et al. |
| 5,195,982 A | 3/1993 | Hoenig |
| 5,248,303 A | 9/1993 | Margolin |
| 5,250,023 A | 10/1993 | Lee et al. |
| 5,279,544 A | 1/1994 | Gross et al. |
| 5,316,013 A | 5/1994 | Striebel et al. |
| 5,527,288 A | 6/1996 | Gross et al. |
| 5,554,131 A | 9/1996 | Lacivita |
| 5,649,910 A | 7/1997 | Kriesel et al. |
| 5,656,032 A | 8/1997 | Kriesel et al. |
| 5,693,018 A | 12/1997 | Kriesel et al. |
| 5,716,343 A | 2/1998 | Kriesel et al. |
| 5,735,818 A | 4/1998 | Kriesel et al. |
| 5,762,634 A | 6/1998 | Davis |
| 5,776,103 A | 7/1998 | Kriesel et al. |
| 5,779,676 A | 7/1998 | Kriesel et al. |
| 5,807,335 A | 9/1998 | Kriesel et al. |
| 5,814,020 A | 9/1998 | Gross |
| 5,830,187 A | 11/1998 | Kriesel et al. |
| 5,848,990 A | 12/1998 | Cirelli et al. |
| 5,848,991 A | 12/1998 | Gross et al. |
| 5,858,001 A | 1/1999 | Tsals |
| 5,858,005 A | 1/1999 | Kriesel |
| 5,885,250 A | 3/1999 | Kriesel et al. |
| 5,906,592 A | 5/1999 | Kriesel et al. |
| 5,921,962 A | 7/1999 | Kriesel et al. |
| 5,922,353 A | 7/1999 | Magruder |
| 5,925,017 A | 7/1999 | Kriesel et al. |
| 5,931,814 A | 8/1999 | Alex et al. |
| 5,957,891 A | 9/1999 | Kriesel et al. |
| 5,957,895 A | 9/1999 | Sage et al. |
| 5,961,492 A | 10/1999 | Kriesel et al. |
| 5,997,501 A | 12/1999 | Gross et al. |
| 6,007,518 A | 12/1999 | Kriesel et al. |
| 6,045,533 A | 4/2000 | Kriesel et al. |
| 6,068,533 A | 5/2000 | Glickman et al. |
| 6,074,369 A | 6/2000 | Sage et al. |
| 6,099,504 A | 8/2000 | Gross et al. |
| 6,126,637 A | 10/2000 | Kriesel et al. |
| 6,132,755 A | 10/2000 | Eicher et al. |
| 6,186,982 B1 | 2/2001 | Gross et al. |
| 6,261,272 B1 | 7/2001 | Gross et al. |
| 6,346,095 B1 | 2/2002 | Gross et al. |
| 6,364,865 B1 | 4/2002 | Lavi et al. |
| 6,371,939 B2 | 4/2002 | Bergens et al. |
| 6,428,517 B1 | 8/2002 | Hochman et al. |
| 6,478,771 B1 | 11/2002 | Lavi et al. |
| 6,500,150 B1 | 12/2002 | Gross et al. |
| 6,530,900 B1 | 3/2003 | Daily et al. |
| 6,562,000 B2 | 5/2003 | Thompson et al. |
| 6,569,143 B2 | 5/2003 | Alchas et al. |
| 6,585,707 B2 | 7/2003 | Cabiri et al. |
| 6,589,229 B1 | 7/2003 | Connelly et al. |
| 6,595,956 B1 * | 7/2003 | Gross ................ A61M 5/14248 128/DIG. 12 |
| 6,611,707 B1 | 8/2003 | Prausnitz et al. |
| 6,641,565 B1 | 11/2003 | Lavi et al. |
| 6,645,081 B1 | 11/2003 | Salas |
| 6,645,181 B1 | 11/2003 | Lavi et al. |
| 6,656,147 B1 | 12/2003 | Gertsek et al. |
| 6,723,068 B2 | 4/2004 | Lavi et al. |
| 6,743,211 B1 | 6/2004 | Prausnitz et al. |
| 6,796,968 B2 | 9/2004 | Ferguson et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,881,203 B2 | 4/2005 | Delmore et al. |
| 6,890,319 B1 | 5/2005 | Crocker |
| 6,905,475 B2 | 6/2005 | Hauschild et al. |
| 6,966,893 B2 | 11/2005 | Holtby et al. |
| 7,014,625 B2 | 3/2006 | Bengtsson |
| 7,186,236 B2 | 3/2007 | Gibson et al. |
| 7,220,244 B2 | 5/2007 | Kriesel et al. |
| 7,226,439 B2 | 6/2007 | Prausnitz et al. |
| 7,250,037 B2 * | 7/2007 | Shermer ................ A61M 5/142 604/134 |
| 7,303,549 B2 | 12/2007 | Flaherty et al. |
| 7,384,413 B2 | 6/2008 | Gross et al. |
| 7,455,663 B2 | 11/2008 | Bikovsky |
| 7,530,964 B2 | 5/2009 | Lavi et al. |
| 7,628,770 B2 | 12/2009 | Ethelfeld et al. |
| 7,637,891 B2 | 12/2009 | Wall |
| 7,670,314 B2 | 3/2010 | Wall et al. |
| 7,678,079 B2 | 3/2010 | Shermer et al. |
| 7,713,234 B2 | 5/2010 | Karanzas |
| 7,766,902 B2 | 8/2010 | Beebe et al. |
| 7,780,636 B2 | 8/2010 | Radmer et al. |
| 7,857,131 B2 | 12/2010 | Vedrine |
| 7,955,297 B2 | 6/2011 | Radmer et al. |
| 7,955,305 B2 | 6/2011 | Moberg et al. |
| 7,981,085 B2 | 7/2011 | Ethelfeld et al. |
| 7,998,117 B2 | 8/2011 | Gross et al. |
| 8,062,253 B2 | 11/2011 | Nielsen et al. |
| 8,110,209 B2 | 2/2012 | Prestrelski et al. |
| 8,162,923 B2 | 4/2012 | Adams et al. |
| 8,167,841 B2 | 5/2012 | Teisen-Simony et al. |
| 8,257,324 B2 | 9/2012 | Prausnitz et al. |
| 8,262,614 B2 | 9/2012 | Freeman et al. |
| 8,298,172 B2 | 10/2012 | Nielsen |
| 8,361,027 B2 | 1/2013 | Gross et al. |
| 8,361,028 B2 | 1/2013 | Gross et al. |
| 8,372,045 B2 | 2/2013 | Needle et al. |
| 8,529,553 B2 | 9/2013 | Mounce et al. |
| 2001/0025168 A1 | 9/2001 | Gross et al. |
| 2002/0095134 A1 | 7/2002 | Pettis et al. |
| 2003/0097098 A1 | 5/2003 | Lavi et al. |
| 2003/0109827 A1 | 6/2003 | Lavi et al. |
| 2003/0135159 A1 | 7/2003 | Daily et al. |
| 2003/0229308 A1 | 12/2003 | Tsals et al. |
| 2004/0059316 A1 | 3/2004 | Smedegaard |
| 2004/0138612 A1 | 7/2004 | Shermer et al. |
| 2005/0038392 A1 | 2/2005 | DeSalvo |
| 2005/0065472 A1 | 3/2005 | Cindrich et al. |
| 2007/0021733 A1 | 1/2007 | Hansen et al. |
| 2007/0049873 A1 | 3/2007 | Hansen et al. |
| 2007/0156094 A1 | 7/2007 | Safabash et al. |
| 2007/0203454 A1 | 8/2007 | Shermer et al. |
| 2007/0299394 A1 | 12/2007 | Rolfe et al. |

(56) References Cited

U.S. PATENT DOCUMENTS

| | | |
|---|---|---|
| 2008/0091139 A1 | 4/2008 | Srinivasan et al. |
| 2008/0215015 A1 | 9/2008 | Cindrich et al. |
| 2010/0100048 A1 | 4/2010 | Nielsen et al. |
| 2011/0098656 A1 | 4/2011 | Burnell et al. |
| 2012/0259281 A1 | 10/2012 | Wei |
| 2012/0310169 A1 | 12/2012 | Sonderegger et al. |
| 2012/0310173 A1 | 12/2012 | Sonderegger |
| 2012/0310175 A1 | 12/2012 | Vedrine et al. |
| 2012/0316506 A1 | 12/2012 | Sonderegger et al. |
| 2012/0323183 A1 | 12/2012 | Peterson et al. |
| 2013/0006195 A1 | 1/2013 | Sonderegger et al. |
| 2013/0006196 A1 | 1/2013 | Sonderegger et al. |
| 2013/0165866 A1 | 6/2013 | Christensen |

FOREIGN PATENT DOCUMENTS

| | | |
|---|---|---|
| CN | 100509069 C | 7/2009 |
| DE | 4039191 C1 | 11/1991 |
| EP | 0850076 B1 | 4/2005 |
| JP | H03-501348 A | 3/1991 |
| JP | 2002505601 A | 2/2002 |
| JP | 2003527932 A | 9/2003 |
| JP | 2006501043 A | 1/2006 |
| JP | 2007105490 A | 4/2007 |
| JP | 2007518455 A | 7/2007 |
| WO | WO-8704631 A1 | 8/1987 |
| WO | WO-9513838 A1 | 5/1995 |
| WO | WO-9710012 A1 | 3/1997 |
| WO | WO-9721457 A1 | 6/1997 |
| WO | WO-9741917 A1 | 11/1997 |
| WO | WO-9857683 A1 | 12/1998 |
| WO | WO-9948546 A1 | 9/1999 |
| WO | WO-0074763 A2 | 12/2000 |
| WO | WO-0172353 A2 | 10/2001 |
| WO | WO-02083214 A1 | 10/2002 |
| WO | WO-2004087240 A1 | 10/2004 |
| WO | WO-2005002649 A1 | 1/2005 |
| WO | WO-2005018705 A2 | 3/2005 |
| WO | WO-2011075101 | 6/2011 |
| WO | WO-2011078851 A1 | 6/2011 |

\* cited by examiner

SELF-INJECTION DEVICE

CROSS-REFERENCE TO RELATED APPLICATIONS

This application is a continuation of U.S. patent application Ser. No. 14/606,935, filed Jan. 27, 2015, which is a continuation of U.S. patent application Ser. No. 13/516,540, filed Aug. 20, 2012, now U.S. Pat. No. 8,961,469, which is a national stage application of International Patent Application No. PCT/US09/06573, filed Dec. 16, 2009. Each of these applications is incorporated herein by reference in its entirety.

FIELD OF THE INVENTION

The present invention relates generally to a substance delivery device having improved patient convenience, ease of use, and efficiency. The present invention also relates generally to a patch-like, self-contained substance infusion or self-injection device that can be used to deliver a variety of substances or medications to a patient. More specifically, the present invention relates to a patch-like infusion or self-injection device with integrated removal of a needle cover and an adhesive release liner.

BACKGROUND OF THE INVENTION

A large number of people, such as those suffering from conditions such as diabetes, use some form of infusion therapy, such as daily insulin infusions, to maintain close control of their glucose levels. Currently, in the insulin infusion treatment example, there are two principal modes of daily insulin therapy. The first mode includes syringes and insulin pens. These devices are simple to use and are relatively low in cost, but they require a needle stick at each injection typically three to four times per day. The second mode includes infusion pump therapy, which entails the purchase of an expensive pump that lasts for about three years. The high cost (roughly 8 to 10 times the daily cost of syringe therapy) and limited lifetime of the pump are high barriers to this type of therapy. Insulin pumps also represent relatively old technology and are cumbersome to use. From a lifestyle standpoint, moreover, the tubing (known as the "infusion set") that links the pump with the delivery site on the patient's abdomen is very inconvenient and the pumps are relatively heavy, making carrying the pump a burden. From a patient perspective, however, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer glucose control and an improved feeling of wellness.

Interest in better therapy is on the rise, accounting for the observed growth in pump therapy and increased number of daily injections. In this and similar infusion examples, what is needed to fully meet this increased interest is a form of insulin delivery or infusion that combines the best features of daily injection therapy (low cost and ease of use) with those of the insulin pump (continuous infusion and precision dosing) and that also avoids the disadvantages of each.

Several attempts have been made to provide ambulatory or "wearable" drug infusion devices that are low in cost and convenient to use. Some of these devices are intended to be partially or entirely disposable. In theory, devices of this type can provide many of the advantages of an infusion pump without the attendant cost and inconvenience. Unfortunately, however, many of these devices suffer from disadvantages including patient discomfort (due to the gauge and/or length of injection needle used), compatibility and interaction between the substance being delivered and the materials used in the construction of the infusion device, and possible malfunctioning if not properly activated by the patient (for example, "wet" injections resulting from premature activation of the device). Difficulties in manufacturing and in controlling needle penetration depth have also been encountered, particularly when short and/or fine-gauge injection needles are used. The possibility of needle-stick injuries to those who come into contact with the used device has also been problematic.

Accordingly, a need exists for an alternative to current infusion devices, such as infusion pumps for insulin, that further provides simplicity in manufacture and use improvements for insulin and non-insulin applications.

SUMMARY OF THE INVENTION

An aspect of the present invention is to provide a patch-like infusion or self-injection device that can be conveniently worn against the skin while providing infusion of a desired substance, and providing minimal discomfort by using one or more microneedles. An additional aspect of the present invention is to provide such an infusion or self-injection device in which removal of a needle cover and an adhesive release liner of such an infusion or self-injection device can be integrated into a single operation.

The foregoing and/or other aspects of the present invention are achieved by providing a drug delivery device, including a body having a reservoir disposed therein for containing a medicament and an injection needle for penetrating the skin of a patient, the needle providing a path for the medicament between the reservoir and the patient. The device also includes a needle cover for selectively covering the injection needle, an adhesive for selectively adhering the device to the patient, a release liner for selectively covering a patient side of the adhesive, and a connecting means for connecting the needle cover and the release liner such that removal of one of the needle cover and the release liner from the device removes the other one of the needle cover and the release liner from the device.

The foregoing and/or other aspects of the present invention are also achieved by providing a drug delivery device, including an injection needle for penetrating the skin of a patient, an adhesive for selectively adhering the device to the patient, a release liner for selectively covering a patient side of the adhesive, the release liner having an opening therein, and a needle cover for selectively covering the injection needle. The needle cover includes a needle-covering portion with a flange larger than the release liner opening, a middle portion positioned adjacent to the flange and being smaller than the release liner opening, and a retaining portion positioned adjacent to the middle portion and having a portion thereof larger than the release liner opening, for retaining the release liner on the middle portion.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, of which.

DETAILED DESCRIPTION OF EXEMPLARY EMBODIMENTS

Figure 1:
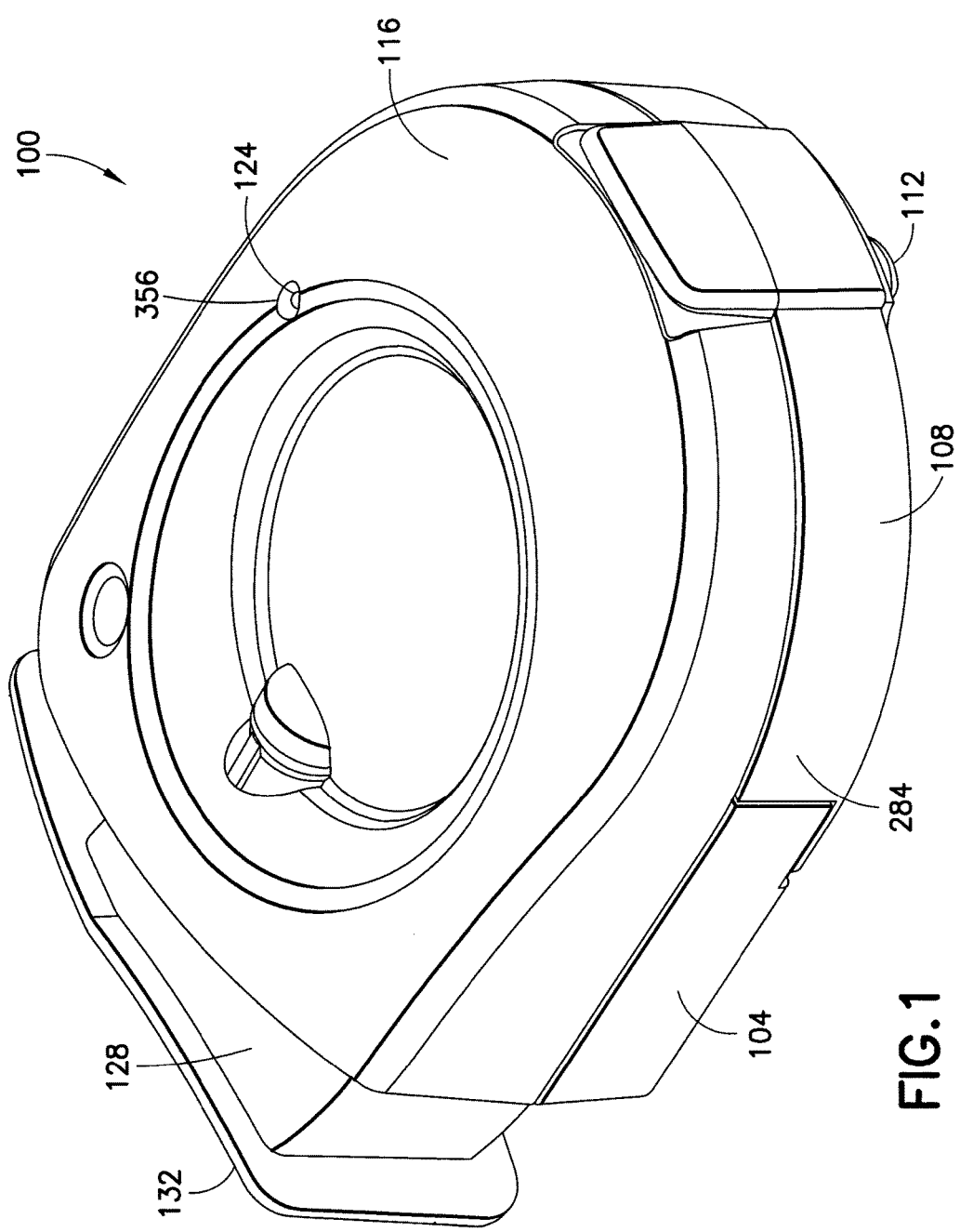
FIG. 1 illustrates a perspective view of an embodiment of a patch-like infusion or self-injection device in a pre-activated state prior to activation.
Figure 2:
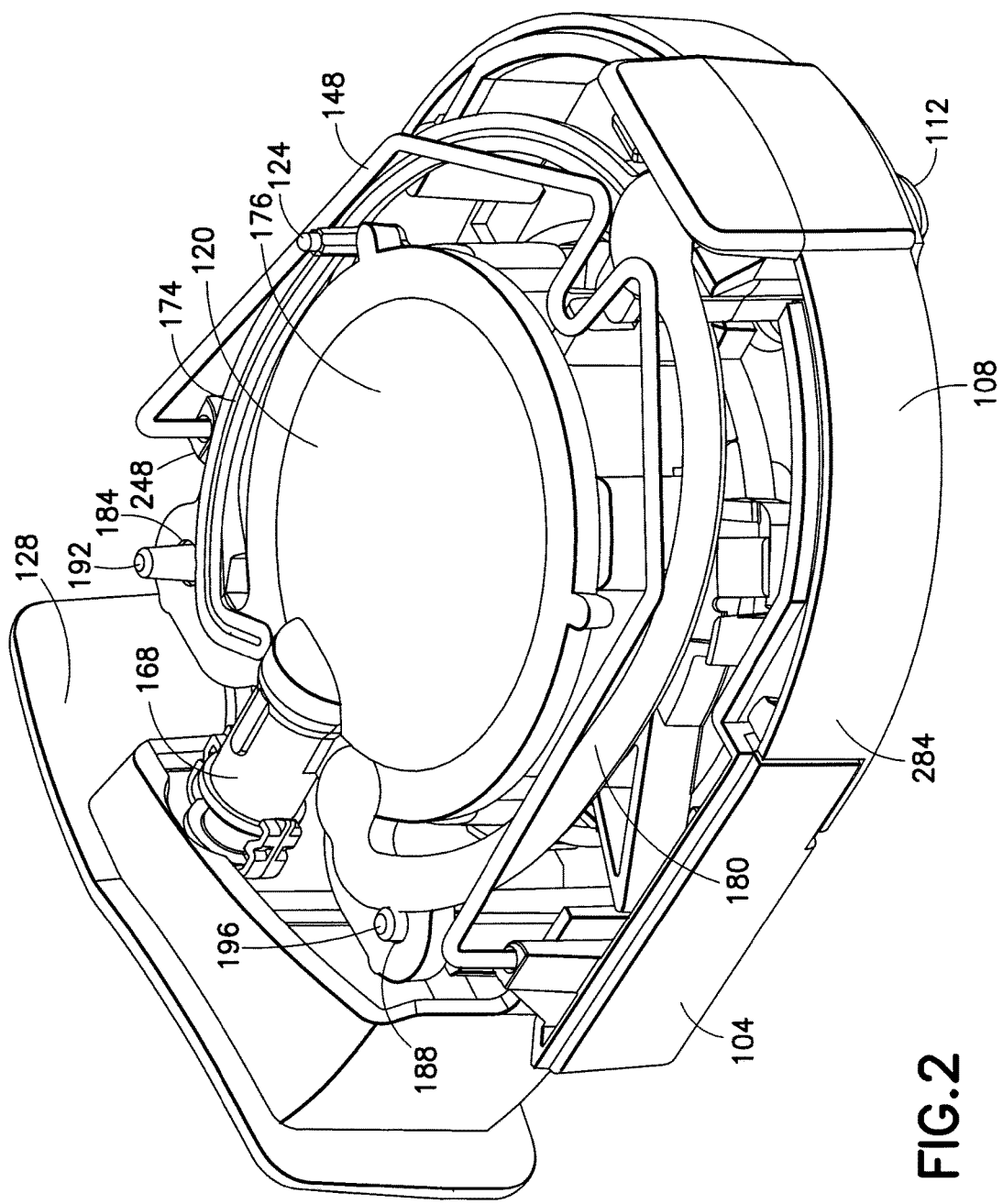
FIG. 2 illustrates a partially exploded view of the infusion device of FIG. 1 in the pre-activated state.

Reference will now be made in detail to embodiments of the present invention, examples of which are illustrated in the accompanying drawings, wherein like reference numerals refer to the like elements throughout. The embodiments described exemplify the present invention by referring to the drawings.

The embodiments of the present invention described below can be used as a convenient, patch-like infusion or self-injection device 100 to deliver a pre-measured dose of a substance, such as a liquid drug or medication, to a patient over a period of time or all at once. The device is preferably provided to the end user in a pre-filled condition, that is, with the drug or medication already in the device reservoir. Though the patch-like infusion or self-injection device 100 (shown, for example, in FIG. 1) described herein can be employed by a patient and/or a caregiver, for convenience, a user of the device is hereinafter referred to as a "patient." Additionally, for convenience, terms such as "vertical" and "horizontal" and "top" and "bottom" are employed to represent relative directions with respect to an infusion device 100 disposed on a horizontal surface. It will be understood, however, that the infusion device 100 is not limited to such an orientation, and that the infusion device 100 may be employed in any orientation. Further, the alternative use of the terms "infusion device" and "self-injection device" to describe devices embodying the present invention is not intended in a limiting sense. Infusion devices that do not have a self-injection capability are within the scope of the present invention, as are self-injection devices that do not carry out continuous infusion. For convenience, but not by way of limitation, the term "infusion device" is used in the description that follows.

The patch-like infusion device 100 of FIG. 1 is self-contained and is attached to the skin surface of the patient by adhesive disposed on a bottom surface of the infusion device 100 (as will be described in greater detail below). Once properly positioned and activated by the patient, the pressure of a released spring on a flexible reservoir within the device can be used to empty the contents of the reservoir through one or more patient needles (for example, microneedles) via a needle manifold. The substance within the reservoir is then delivered through the skin of the patient by the microneedles, which are driven into the skin. It will be understood that other embodiments are possible in which the spring is replaced with a different type of stored energy device, which may be mechanical, electrical and/or chemical in nature.

As will be appreciated by one skilled in the art, there are numerous ways of constructing and using the patch-like infusion device 100 disclosed herein. Although reference will be made to the embodiments depicted in the drawings and the following descriptions, the embodiments disclosed herein are not meant to be exhaustive of the various alternative designs and embodiments that are encompassed by the disclosed invention. In each disclosed embodiment, the device is referred to as an infusion device, but the device may also inject substances at a much faster (bolus) rate than is commonly accomplished by typical infusion devices. For example, the contents can be delivered in a period as short as several seconds or as long as several days.

Figure 5:
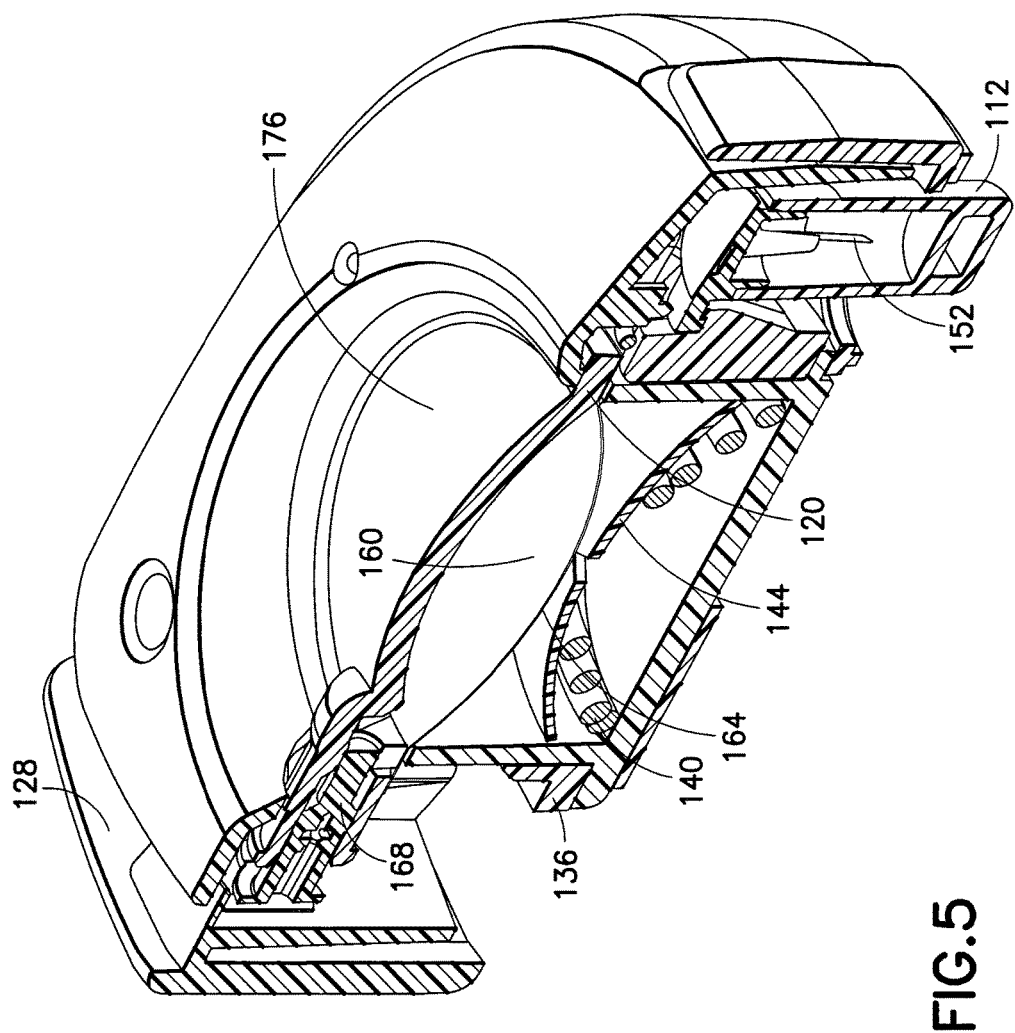
FIG. 5 illustrates a cross-sectional view of the infusion device of FIG. 1 in the pre-activated state.
Figure 6:
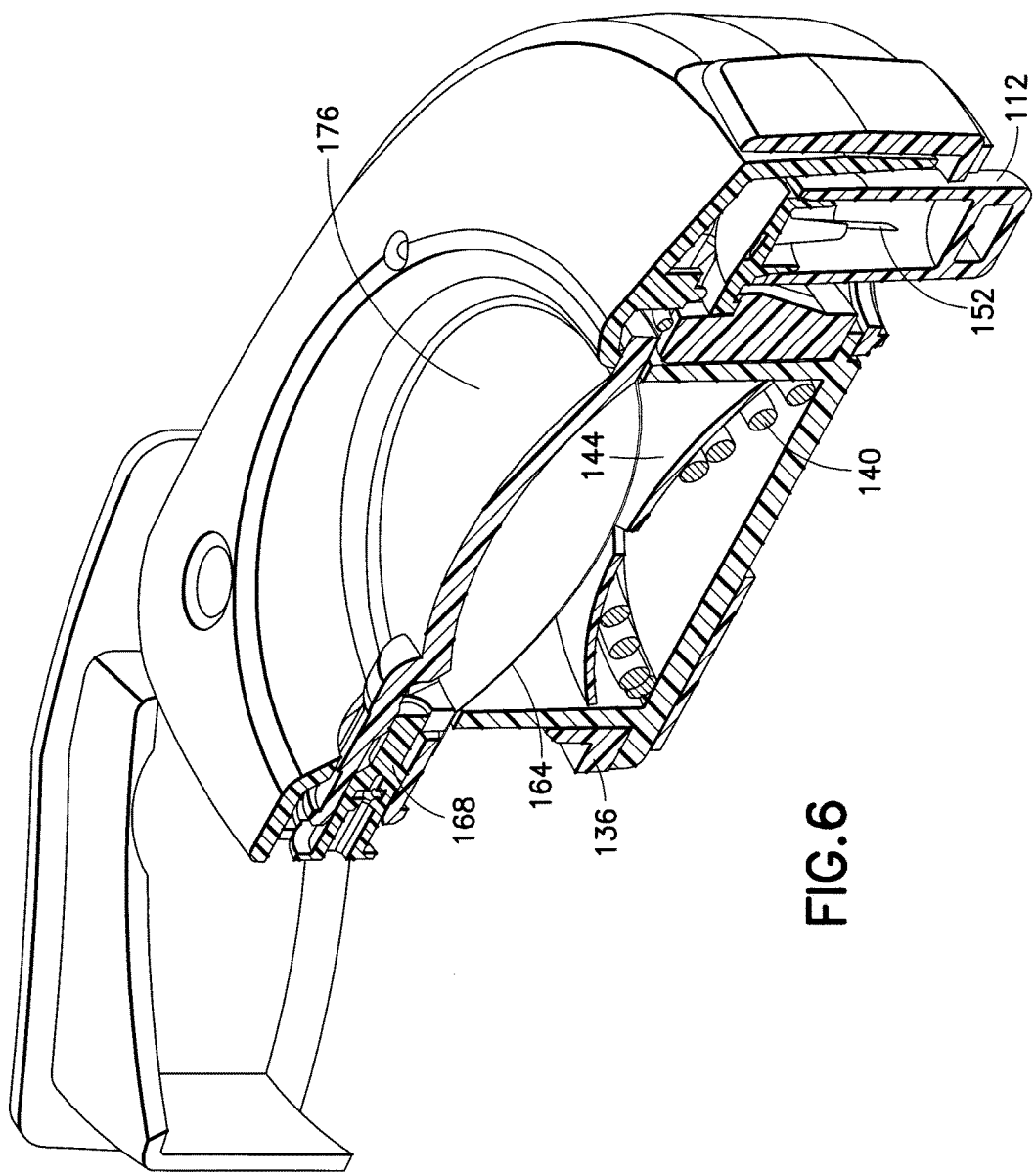
FIG. 6 illustrates a cross-sectional view of the infusion device of FIG. 1 in the pre-activated state with the activator button rotated away.
Figure 7:
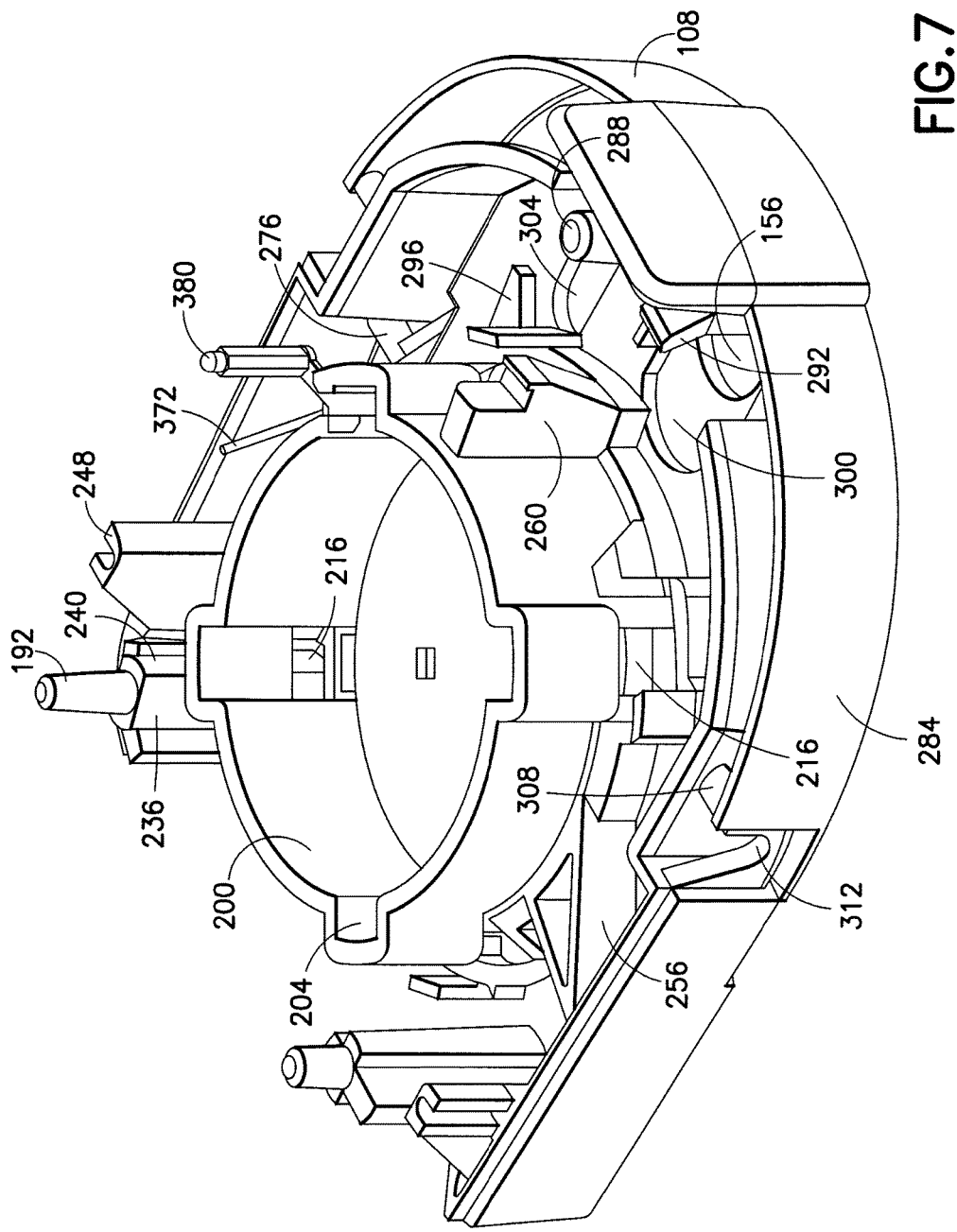
FIG. 7 illustrates a partially exploded view of the infusion device of FIG. 1 during installation of a safety mechanism.
Figure 8:
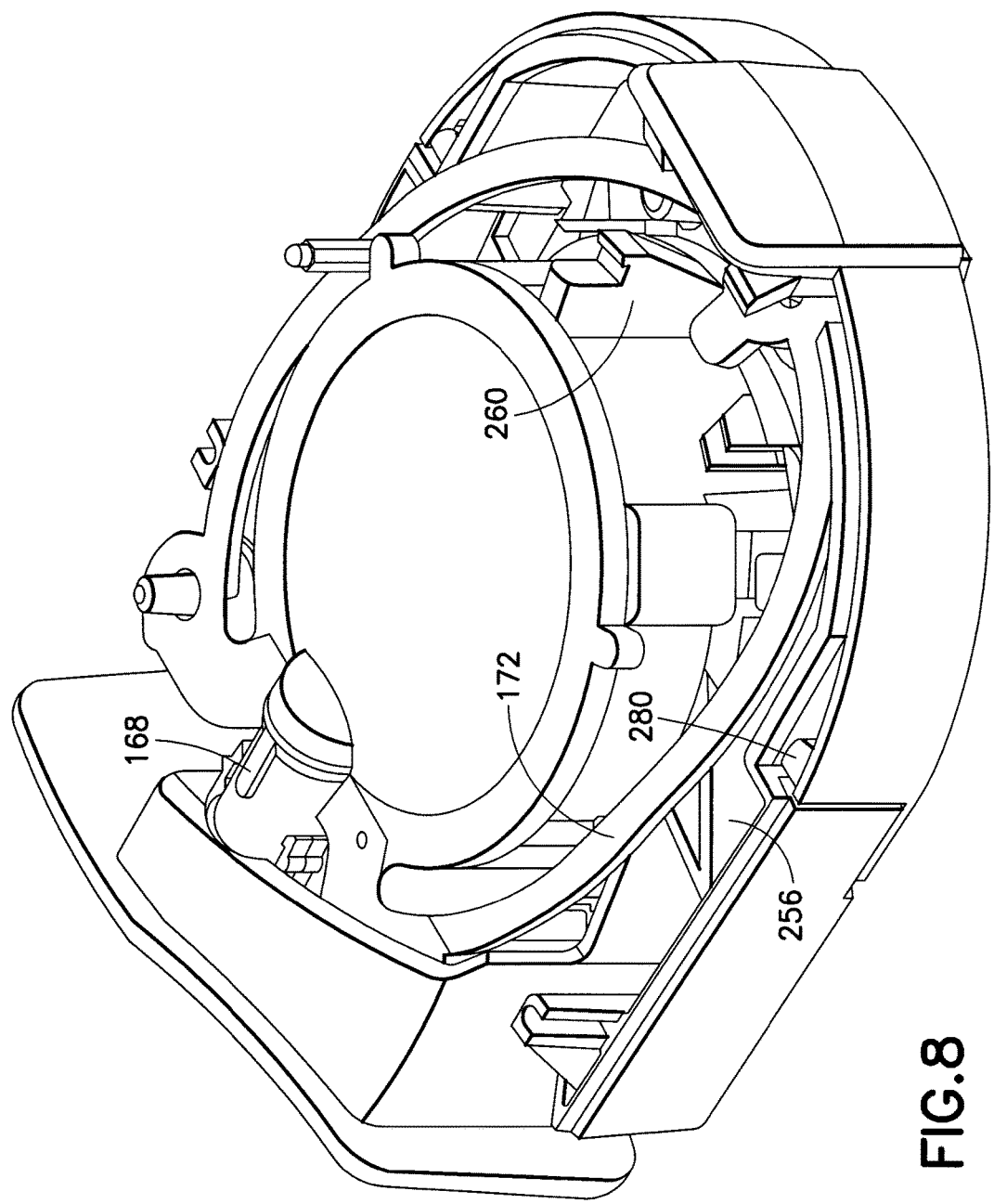
FIG. 8 illustrates a partially exploded view of the infusion device of FIG. 1 subsequent to activation.
Figure 9:
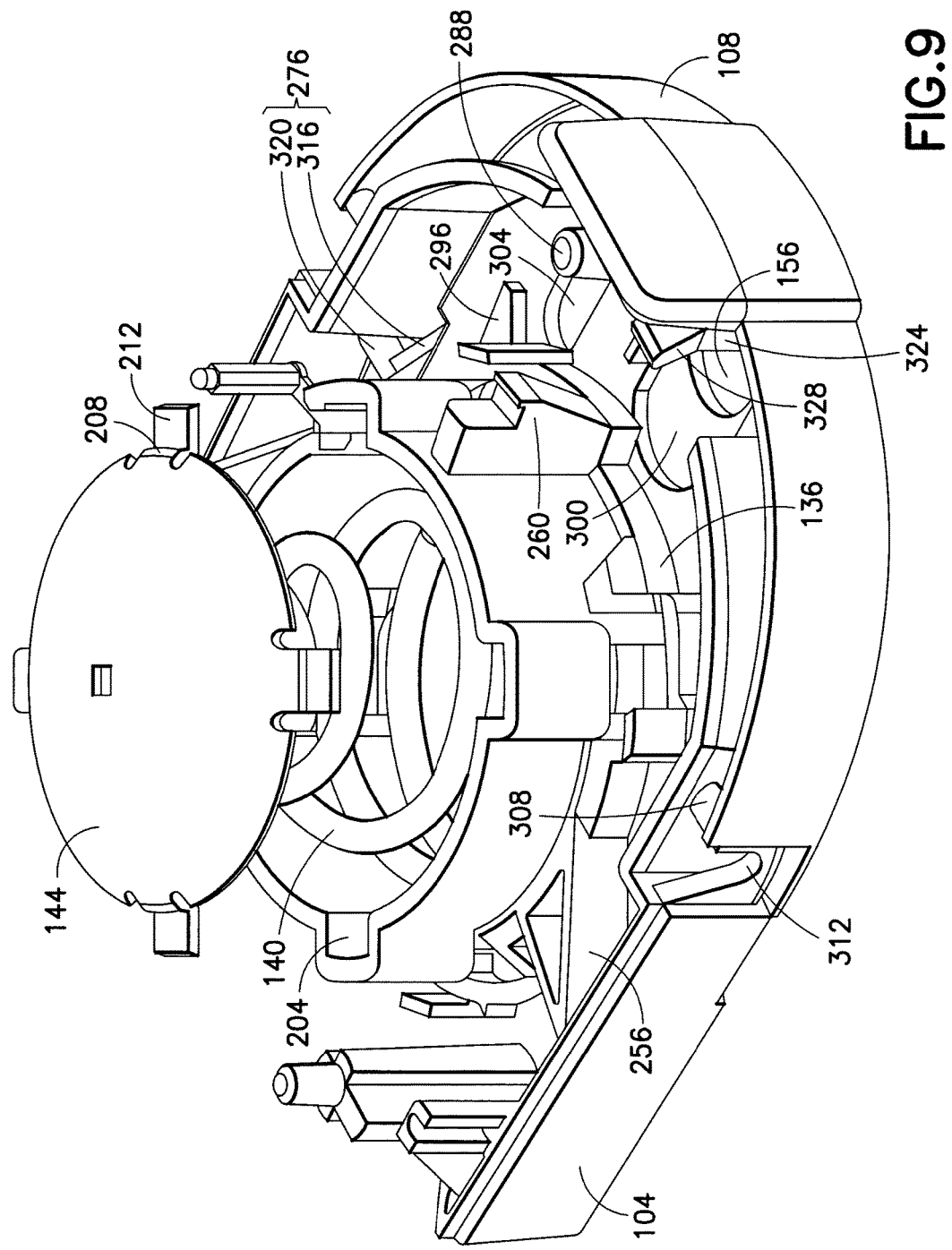
FIG. 9 illustrates a more fully exploded view of the infusion device of FIG. 1 subsequent to activation.
Figure 10:
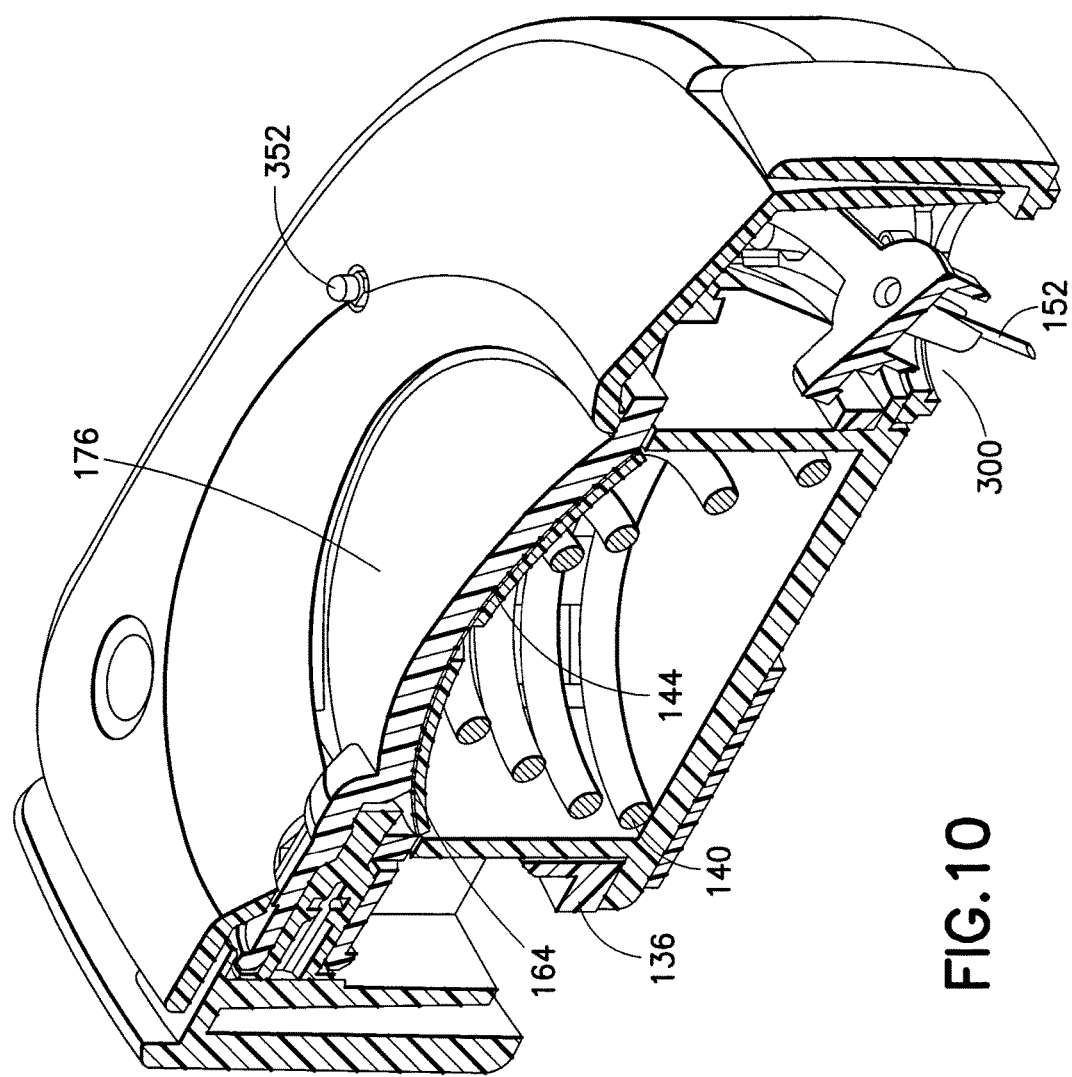
FIG. 10 illustrates a cross-sectional view of the infusion device of FIG. 1 subsequent to activation.
Figure 11:
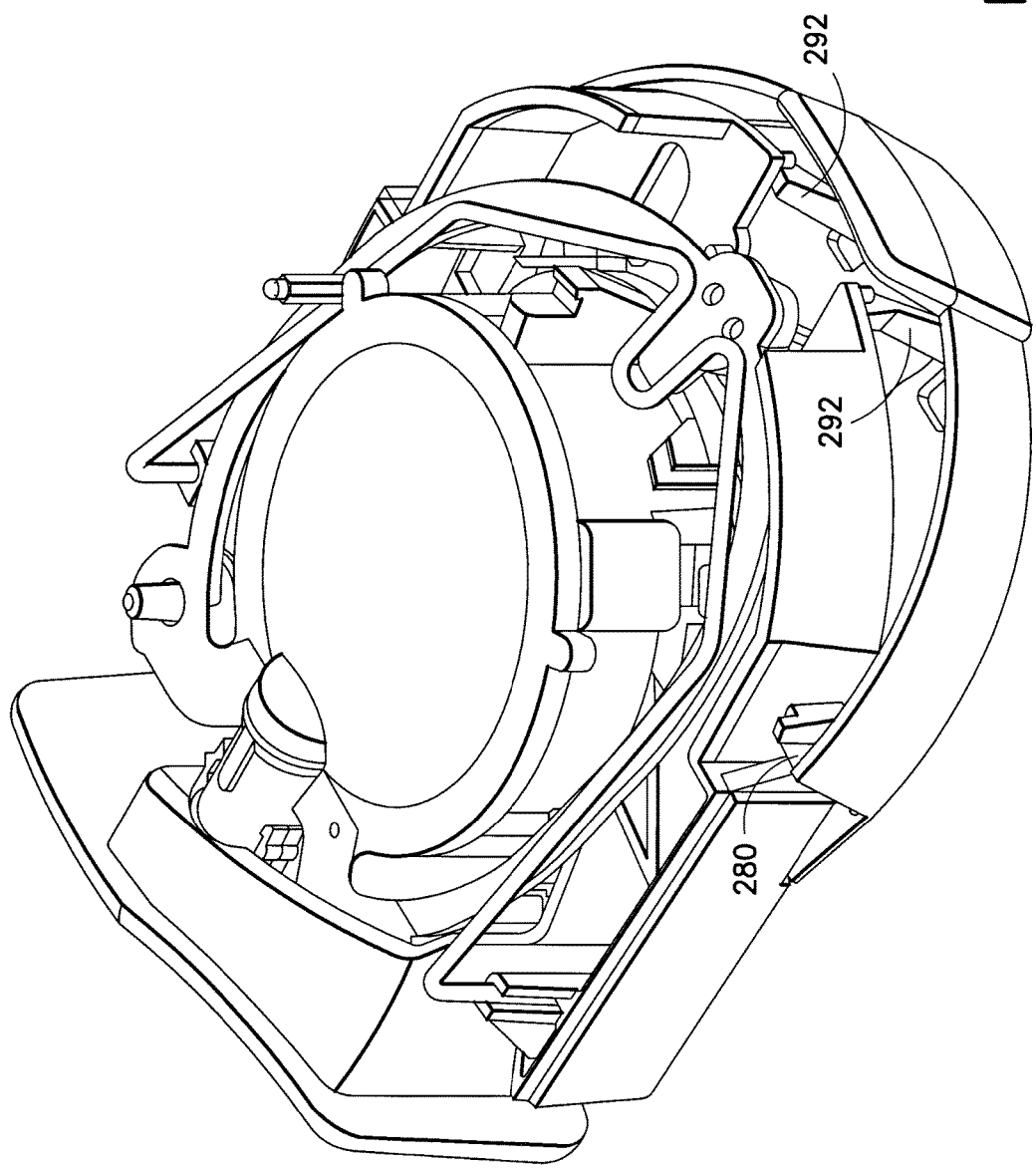
FIG. 11 illustrates a partially exploded view of the infusion device of FIG. 1 subsequent to deployment of the safety mechanism.
Figure 12:
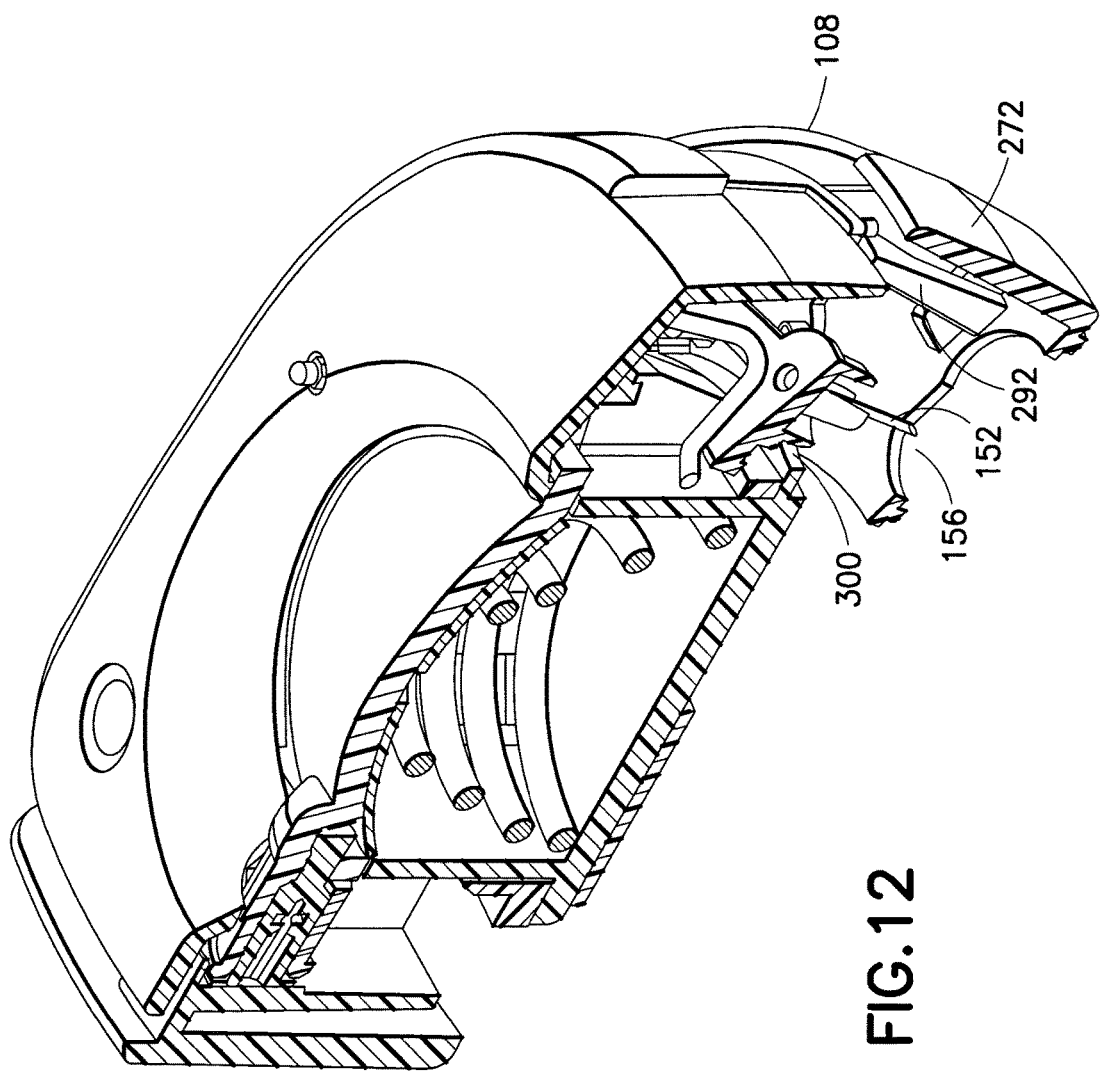
FIG. 12 illustrates a cross-sectional view of the infusion device of FIG. 1 subsequent to deployment of the safety mechanism.

In an embodiment of the device shown in FIGS. 1 through 12, a push-button design of the patch-like infusion device 100 is shown wherein the activation and energizing of the device is accomplished in a single multi-function/step process. FIG. 1 illustrates an assembled embodiment of the infusion device 100 in a pre-activated state. FIGS. 2-6 illustrate partially exploded and cross-sectional views of the infusion device 100 in the pre-activated state, FIG. 7 illustrates a partially exploded view of the infusion device 100 during installation of a safety mechanism, FIGS. 8-10 illustrate exploded and cross-sectional views of the infusion device 100 subsequent to activation, and FIGS. 11 and 12 illustrate exploded and cross-sectional views of the infusion device 100 subsequent to deployment of the safety mechanism. The infusion device 100 is configured to operate between the pre-activated state (shown, for example, in FIGS. 1, 2, and 5), an activated or fired state (shown, for example, in FIGS. 8-10), and a retracted or safe state (shown, for example, in FIGS. 11 and 12).

As shown in FIG. 1, an embodiment of the patch-like infusion device 100 includes a bottom enclosure 104, a safety mechanism 108, a flexible needle-covering portion 112 of a needle cover 114, a top enclosure 116, a reservoir subassembly 120, an end-of-dose indicator (EDI) 124, and an activator button 128, which includes a patient interface surface 132. Additionally, as shown in FIGS. 2-6, the infusion device 100 also includes a rotor or activation ring 136, a pressurization spring 140, a dome-like metal plunger 144, and a drive spring 148.

The flexible needle-covering portion 112 provides patient and device safety by protecting at least one needle 152 (described in greater detail below) and providing a sterile barrier. The needle-covering portion 112 protects the needle 152 during device manufacture, protects the patient prior to use, and provides a sterility barrier at any point prior to removal. According to one embodiment, the needle-covering portion 112 is attached via a press fit with a needle manifold in which the at least one needle 152 is disposed. Additionally, according to one embodiment, a needle opening 156 (described in greater detail below) of the safety mechanism 108 is shaped to closely correspond to a perimeter of the needle-covering portion 112.

As shown, for example, in FIGS. 2, 3, 5, 6, 8, 10, and 12, the reservoir subassembly 120 includes a reservoir 160, a reservoir dome seal 164, a valve 168, at least one needle 152, and at least one channel 172 (see, for example, FIG. 8) disposed between the valve 168 and the needle 152 and creating a flow path therebetween. The reservoir 160 includes a dome 176. Additionally, the reservoir subassembly 120 includes the removable needle-covering portion 112 to selectively cover the at least one needle 152. According to one embodiment, the reservoir subassembly 120 also includes a reservoir arm seal 180, covering the channel 172. Preferably, the needle 152 includes a needle manifold and a plurality of microneedles 152.

The reservoir dome seal (flexible film) 164 of the reservoir subassembly 120, as shown, for example, in FIG. 5, is disposed between the plunger 144 and the dome 176. Reservoir contents (for example, medicinal material) for the infusion device 100 are disposed in the space between the reservoir dome seal 164 and the dome 176. The combination of the reservoir dome seal 164, the dome 176, and the space therebetween defines a reservoir 160. The dome 176 is preferably transparent to permit viewing of the reservoir contents. The reservoir dome seal 164 can be made of non-distensible materials or laminates, such as metal-coated films or other similar substances. For example, one possible flexible laminate film that can be used in the reservoir dome seal 164 includes a first polyethylene layer, a second chemical layer as known to those skilled in the art to provide an attachment mechanism for a third metal layer which is chosen based upon barrier characteristics, and a fourth layer that includes polyester and/or nylon. By utilizing a metal-coated or metallized film in conjunction with a rigid portion (for example, dome 176), the barrier properties of the reservoir 160 are improved, thereby increasing or improving the shelf life of the contents contained within. For example, where a reservoir content includes insulin, the primary materials of contact in the reservoir 160 include linear, low-density polyethylene (LLDPE), low-density polyethylene (LDPE), cyclic olefin copolymer (COC) and Teflon. As described in greater detail below, the primary materials of contact in the remaining flow path of the reservoir contents may also include COC and LLDPE, as well as thermoplastic elastomer (TPE), medical grade acrylic, stainless steel, and a needle adhesive (e.g. a UV cured adhesive). Such materials that remain in extended contact with the contents of the reservoir 160 preferably pass ISO 10-993 and other applicable biocompatibility testing.

The reservoir subassembly 120 is further preferably able to be stored for the prescribed shelf life of the reservoir contents in applicable controlled environments without adverse effect to the contents, and is capable of applications in a variety of environmental conditions. Additionally, the barrier provided by the components of the reservoir subassembly 120 do not permit the transport of gas, liquid, and/or solid materials into or out of the contents at a rate greater than that allowable to meet the desired shelf life. In the embodiments shown above, the reservoir materials are capable of being stored and operated in a temperature range of approximately 34 to 120 degrees Fahrenheit and can have a shelf life of two or more years.

In addition to satisfying stability requirements, the reservoir subassembly 120 can further ensure operation by successfully passing any number of leak tests, such as holding a 30 psi sample for 20 minutes without leaking. Additional filling, storage and delivery benefits resulting from the configuration of the reservoir include minimized headspace and adaptability as described in greater detail below.

In one embodiment, the reservoir 160 is evacuated prior to filling. By evacuating the reservoir 160 prior to filling and having only a slight depression in the dome 176, headspace and excess waste within the reservoir 160 can be minimized. In addition, the shape of the reservoir can be configured to adapt to the type of energizing mechanism (for example, pressurization spring 140 and plunger 144) used. Additionally, using an evacuated flexible reservoir 160 during filling minimizes any air or bubbles within the filled reservoir 160. The use of a flexible reservoir 160 is also very beneficial when the infusion device 100 is subjected to external pressure or temperature variations, which can lead to increased internal reservoir pressures. In such case, the flexible reservoir 160 expands and contracts with the reservoir contents, thereby preventing possible leaks due to expansion and contraction forces.

Yet another feature of the reservoir 160 includes the ability to permit automated particulate inspection at the time of filling, or by a patient at the time of use. One or more reservoir barriers, such as the dome 176, can be molded of a transparent, clear plastic material, which allows inspection of the substance contained within the reservoir. The transparent, clear plastic material is preferably a cyclic olefin copolymer that is characterized by high transparency and clarity, low extractables, and biocompatibility with the substance contained in the reservoir 160. A suitable material is available from Zeon Chemicals, L.P., of Louisville, Ky. under the designation "BD CCP Resin," and is listed by the U.S. Food and Drug Administration and DMF No. 16368. In such applications, the reservoir 160 includes minimal features that could possibly obstruct inspection (i.e. rotation during inspection is permitted).

Channel arm 172 is provided in the form of at least one flexible arcuate arm extending from the valve 168 to the needle manifold or microneedles 152. The arcuate arm has a groove 174 (see, for example, FIG. 2) formed therein. To provide a fluid path between valve 168 and the needle manifold or microneedles 152, the reservoir arm seal 180 covers the groove 174. The fluid path (disposed in channel arm 172—shown, for example, in FIG. 8) between the reservoir 160 and the microneedles 152 is constructed of materials similar or identical to those described above for the reservoir 160. For example, channel arm 172 may be constructed of the same material as the dome 160 and the reservoir arm seal 180 may constructed of the same material as the reservoir dome seal 164. According to one embodiment, both channel arms 172 are employed as fluid paths between the valve 168 and the needle manifold or microneedles 152. According to another embodiment, only one of the channel arms 172 is employed as a fluid path, and the remaining channel arm 172 provides structural support. In such an embodiment, the groove 174 extends fully from the valve 168 to the needle manifold or microneedles 152 only in the channel arm 172 that will be employed as the fluid path.

The channel arm 172 must be sufficiently flexible to withstand the force of activation. Contrasting the position of the channel arm 172 in FIGS. 2 and 8, the channel arm 172 (covered by reservoir arm seal 180 in FIG. 2, which is removed in FIG. 8 for clarity) elastically deforms when the microneedles 152 are driven into the patient's skin (described in greater detail below). During such deformation, the channel arm 172 must maintain the integrity of the fluid path between the valve 168 and the needle manifold or microneedles 152. Additionally, the materials for the channel arm 172 satisfy numerous biocompatibility and storage tests. For example, as shown in Table 1 below, where an infusion device content includes insulin, the primary materials of contact in the reservoir 160 include linear, low-density polyethylene, cyclic olefin copolymer, and Teflon, and can also include a transparent, clear plastic. The primary materials of contact in the remaining flow path (channel 62) between the reservoir 160 and the microneedles 152 of the needle manifold include COC and/or medical grade acrylic, LLDPE, TPE, and stainless steel, as well as the needle adhesive.

TABLE 1

| Path Component | Material |
| --- | --- |
| Reservoir | Polyethylene, cyclic olefin copolymer, and/or Teflon |
| Reservoir Dome Seal | Metal-coated film, such as polyethylene, aluminum, polyester, and/or nylon with a chemical tie layer |
| Valve | TPE |
| Needle Manifold | COC and/or medical grade acrylic |
| Needle adhesive | UV-cured adhesive |
| Microneedle | Stainless steel |

More specifically, the microneedles 152 can be constructed of stainless steel, and the needle manifold can be constructed of polyethylene and/or medical grade acrylic. Such materials, when in extended contact with the contents of the reservoir, preferably pass ISO 10-993 biocompatibility testing.

The valve 168, disposed between the reservoir 160 and the channel 172, selectively permits and restricts fluid flow between the reservoir 160 and the channel 172. The valve 168 moves between a pre-activated position (shown, for example, in FIGS. 2, 3, and 6) and an activated position (shown, for example, in FIGS. 8-10). When in the activated position, the valve permits fluid flow between the reservoir 160 and the channel 172, and therefore to the needle manifold and microneedles 152.

In use, the valve 168 will eventually be pushed into the activated position by the movement of the activator button 128, best illustrated by the movement of the valve 168 between FIGS. 5 and 10. As shown in FIG. 10, the movement of the valve 168 advances the enlarged distal end of the valve 168, thereby permitting the drug to flow from the reservoir 160 into the channel 172 and down the fluid path to the needle manifold.

The embodiment described above includes at least one needle 152, or microneedle 152, but may contain several, such as the two illustrated microneedles 152. Each microneedle 152 is preferably at least 31 gauge or smaller, such as 34 gauge, and is anchored within a patient needle manifold that can be placed in fluid communication with the reservoir 160. The microneedles 152, when more than one is included in the infusion device 100, can also be of differing lengths, or gauges, or a combination of both differing lengths and gauges, and can contain one or more ports along a body length, preferably located near the tip of the microneedle 152 or near the tip bevel if any of the microneedles 152 has one.

According to one embodiment, the gauge of the microneedles 152 governs the delivery rate of reservoir contents of the infusion device 100. The use of multiple 34 gauge microneedles 152 to deliver the reservoir contents is practical when the infusion occurs over a longer period than typically associated with an immediate syringe injection requiring a much larger cannula, or needle. In the disclosed embodiments, any microneedles 152 that target either an intradermal or subcutaneous space can be used, but the illustrated embodiments include intradermal microneedles 152 of between 1 and 7 mm in length (i.e., 4 mm). The arrangement of the microneedles 152 can be in a linear or nonlinear array, and can include any number of microneedles 152 as required by the specific application.

As noted above, the microneedles 152 are positioned in a needle manifold. In the needle manifold, at least one fluid communication path, or channel 172, is provided to each microneedle 152. The manifold may simply have a single path to one or more microneedles 152, or may provide multiple fluid paths or channels routing the reservoir contents to each microneedle 152 separately. These paths or channels may further comprise a tortuous path for the contents to travel, thereby affecting fluid pressures and rates of delivery, and acting as a flow restrictor. The channels or paths within the needle manifold can range in width, depth and configuration depending upon application, where channel widths are typically between about 0.015 and 0.04 inch, preferably 0.02 inch, and are constructed to minimize dead space within the manifold.

According to one embodiment, the reservoir subassembly 120 has a pair of holes 184 and 188 to aid registration of the reservoir subassembly 120 with respect to the bottom enclosure 104. First and second posts 192 and 196 (described in greater detail below) of the bottom enclosure 104 are inserted through the respective holes 184 and 188.

Figure 4:
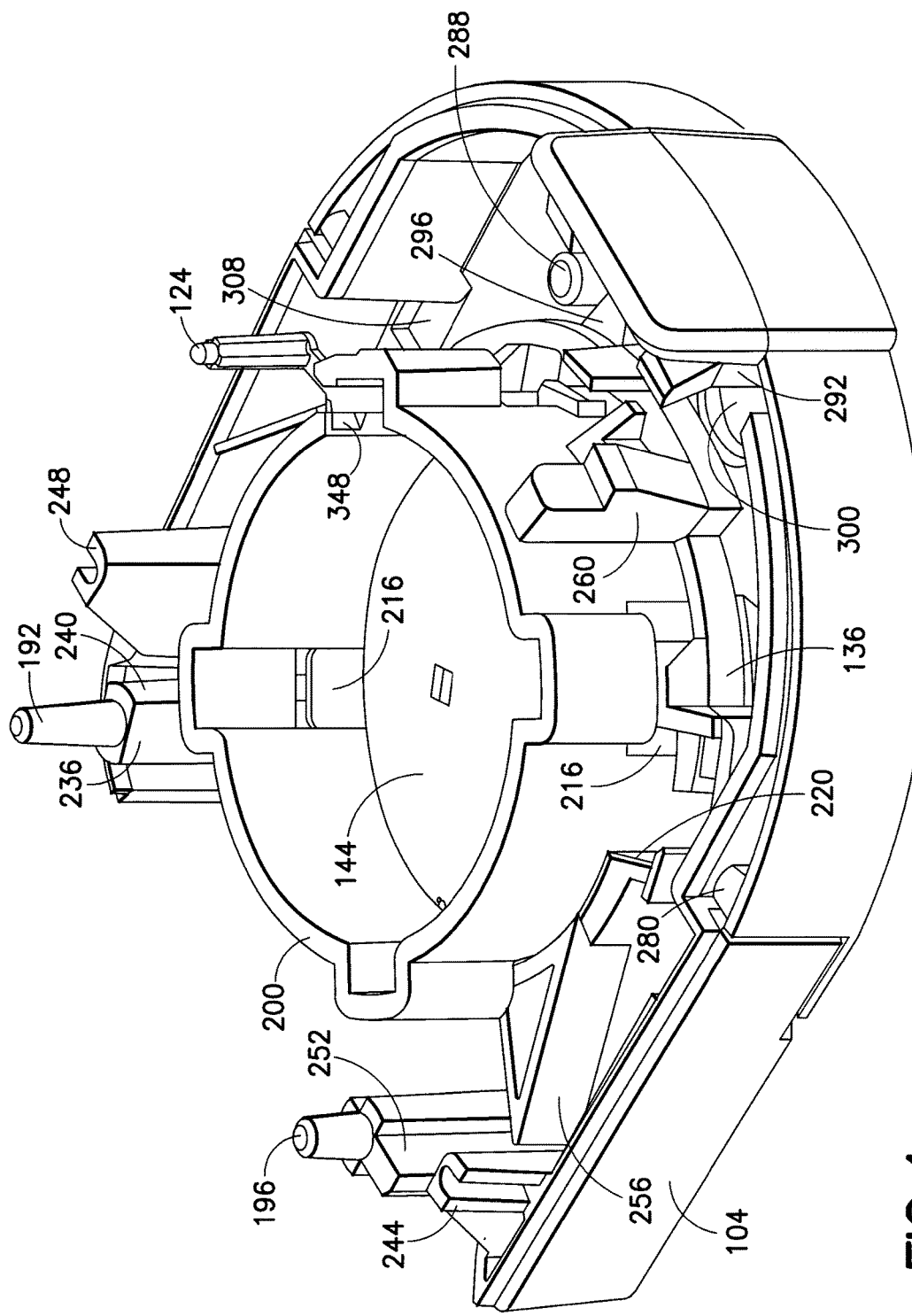
FIG. 4 illustrates a more fully exploded view of the infusion device of FIG. 1 in the pre-activated state.

In exploded views with the reservoir subassembly 120 removed, FIGS. 4, 7, and 9 illustrate that bottom enclosure 104 includes a substantially cylindrical housing 200 in which pressurization spring 140 and plunger 144 are disposed. According to one embodiment, cylindrical housing 200 includes a plurality of recessed channels 204 to guide a respective plurality of legs 208 and feet 212 of the plunger 144 as the plunger translates within the housing 200. Collectively, a leg 208 and a foot 212 constitute a plunger tab 214. As shown in FIGS. 4, 7, and 9, for example, the recessed channels 204 extend only part of the way down the cylindrical housing 200 from a top thereof. Below the recessed channels 204, there are openings 216 through which the feet 212 of plunger 144 can extend outside of the cylindrical housing 200. The openings 216 are substantially L-shaped with horizontal portions at the base of the cylindrical housing 200, and a vertical portion substantially aligned with the recessed channels 204.

When the infusion device 100 is in the pre-activated state, the pressurization spring 140 is compressed by the plunger 144 (as shown, for example, in FIGS. 4-6), and the feet 212 of the plunger 144 are substantially disposed in the horizontal portions of the openings 216. The force of the pressurization spring 140 biases the feet 212 of the plunger 144 against a top of the horizontal portions of the openings 216 (i.e., a ledge of the cylindrical housing 200). Together, as described in greater detail below, the pressurization spring 140 and the plunger 144 form a pressurization system to pressurize the reservoir 160 when the infusion device 100 is activated.

As described in greater detail below, the rotor 136 rotates around the base of the cylindrical housing 200 between a pre-activated position (illustrated, for example, in FIGS. 2-4) and an activated position (illustrated, for example, in FIGS. 8-10). When the rotor 136 rotates from the pre-activated position to the activated position, at least one foot engaging surface 220 (shown, for example, in FIG. 4) of the rotor 136 engages at least one of the feet 212 of the plunger 144 and rotates the plunger 144 so that the feet 212 align with the vertical portions of the openings 216 and the recessed channels 204. At this point, the pressurization spring 140 moves the plunger 144 upward with the feet 212 being guided by the raised channels 204.

The pressurization spring 140 is included in the infusion device 100 to apply an essentially even force to the reservoir 160, to force the contents from the reservoir 160. The pressurization spring 140 is used to store energy that, when released, pressurizes the reservoir 160 at the time of use. The pressurization spring 140 is held in a compressed state by engagement between feet 212 of the plunger 144 and the cylindrical housing 200. This engagement prevents the pressurization spring 140 from putting stress on a film (to be described later) of the reservoir 160 or any remaining device components (other than the bottom enclosure 104 and the plunger 144) during storage. The plunger 144 is sufficiently rigid to resist spring tension and deformation, and should not fail under normal load.

As noted above, when the rotor 136 rotates from the pre-activated position to the activated position, the rotor 136 engages at least one of the feet 212 of the plunger 144 and rotates the plunger 144 to align the feet 212 with the vertical portions of the openings 216 and the recessed channels 204. The compressed pressurization spring 140, then moves the plunger 144 upward, and in doing so, exerts a force on the film of the reservoir 160. The pressurization spring 140 can be configured to preferably create a pressure within the reservoir 116 of from about 1 to 50 psi, and more preferably from about 2 to about 25 psi for intradermal delivery of the reservoir contents. For sub-cutaneous injection or infusion, a range of about 2 to 5 psi may be sufficient.

According to one embodiment, the activator button 128 includes the patient interface surface 132 that the patient presses to activate the infusion device 100. The activator button 128 also includes a hinge arm 224 and an activation arm 228 (both shown, for example, in FIG. 3). The hinge arm 224 of the activator button 128 includes a cylindrical portion with an opening. The activation arm 228 includes a tab 230 (see, for example, FIG. 3). According to one embodiment, the tab 230 includes a bearing surface 232 and a locking surface 234 disposed adjacent to the cantilevered end of the bearing surface 232. According to one embodiment, the tab 230 forms an acute angle with a main portion of the activation arm 228.

The first post 192, disposed on the bottom enclosure 104, extends upwardly therefrom. According to one embodiment (as shown, for example, in FIGS. 4 and 7), a base of the first post 192 includes a pair of flat sides 236 and a pair of rounded sides 240. Additionally, as shown, for example, in FIGS. 4 and 7, the second post 196 and first and second drive spring bases 244 and 248 extend upwardly from the bottom enclosure 104. As will be described in greater detail below, the first and second drive spring bases 244 and 248 anchor respective ends of drive spring 148. The first drive spring base 244 is disposed adjacent to the second post 196 with a space therebetween.

Figure 3:
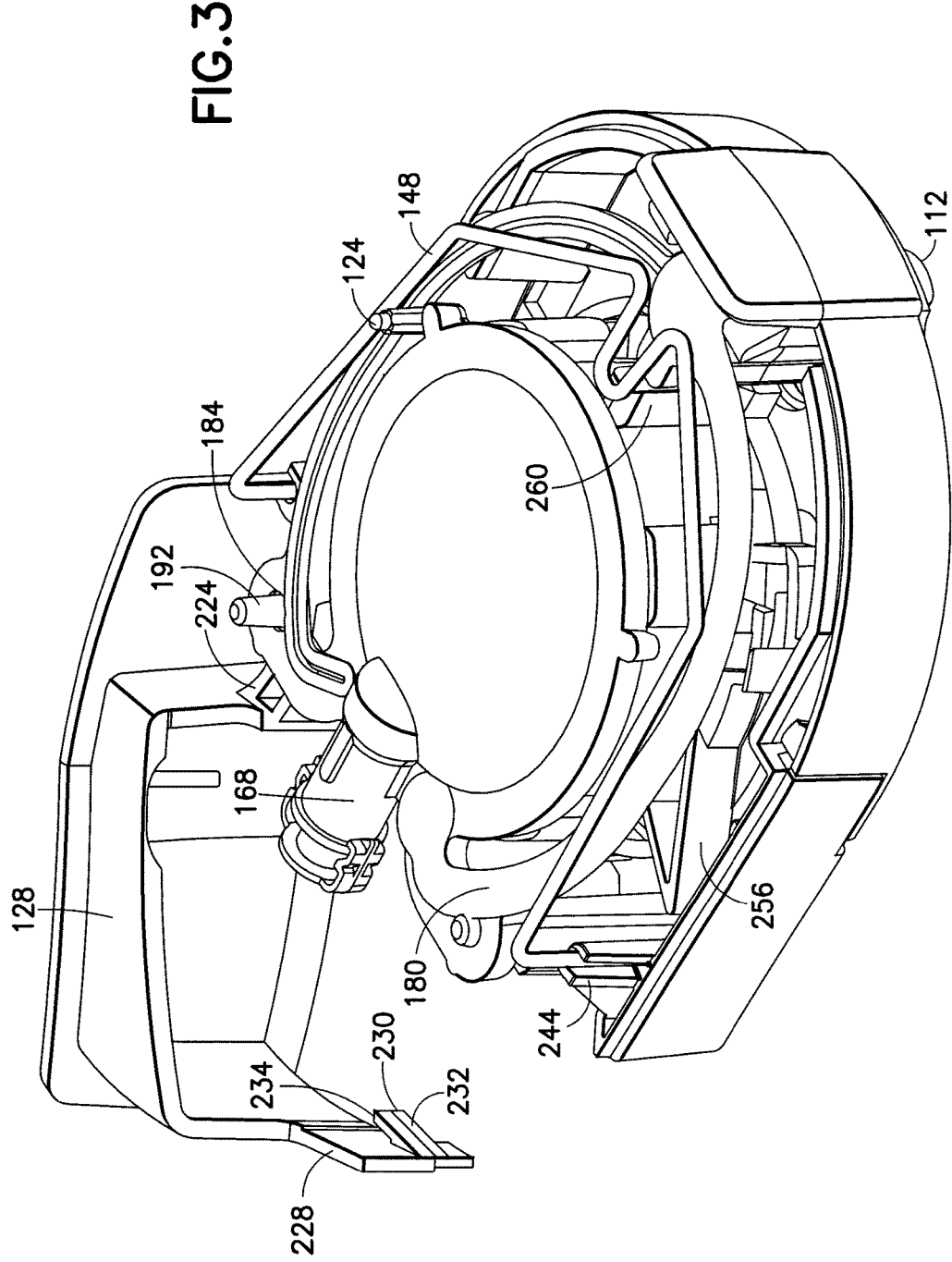
FIG. 3 illustrates a partially exploded view of the infusion device of FIG. 1 in the pre-activated state with an activator button rotated away to reveal more detail.

According to one embodiment, FIGS. 3 and 6 illustrate the positioning of the activator button 128 with respect to the bottom enclosure 104, for assembly of the activator button 128. In this position, the opening of the cylindrical portion of the hinge arm 224 allows the activator button 128 to slide horizontally (passing the flat sides 236) and engage the first post 192. The hinge arm 224 (and therefore the activator button 128) can then rotate about the first post 192. As the activation arm 228 passes into the space between the second post 196 and the first drive spring base 244, at least one of the tab 230 and the activation arm 228 elastically deforms until a cantilevered end of the bearing surface 232 of tab 230 passes a retaining face 252 of the second post 196. The passage of the cantilevered end of the bearing surface 232 of tab 230 past the retaining face 252 (see, for example, FIG. 4) of the second post 196 and the engagement of the locking surface 234 of tab 230 with the retaining face 252 provides an audible click and tactile feedback conveying that the activator button 128 is in the pre-activated position.

Referring back to FIGS. 2-4, and 7-9, rotor 136 additionally includes an activation projection 256 and a drive spring holder 260. The activation arm 228 of the activator button 128 engages the activation projection 256 when a patient depresses the activator button 128, thereby rotating the rotor 136 from the pre-activated position to the activated position.

The drive spring holder 260 maintains the drive spring 148 in a pre-activated position when the rotor 136 is in the pre-activated position. As noted previously, the first and second drive spring bases 244 and 248 anchor opposing ends of the drive spring 148. At approximately a midpoint of the drive spring 148, there is a substantially U-shaped projection as shown, for example, in FIGS. 2 and 3, for engagement with the drive spring holder 260 of the rotor 136. Accordingly, when the rotor 136 is in the pre-activated position and the drive spring 148 engages the drive spring holder 260, the drive spring 148 is maintained in a tensile state. And when the drive spring holder 260 releases the drive spring 148 (i.e., when the rotor rotates from the pre-activated position to the activated position as illustrated, for example, in FIGS. 8-10), the drive spring 148 drives the microneedles 152 to extend outside of the infusion device 100 through an opening 300 in the bottom enclosure 104 (and through an opening in the safety mechanism 108 described in greater detail below).

Thus, as will be described in greater detail below, the activation and energizing of the infusion device 100 that is accomplished in a single multi-function/step process includes depression of the activator button 128 by a patient, and rotation of the rotor 136 due to engagement between the activation arm 228 of the activator button 128 and the activation projection 256 of the rotor 136. As described above, the rotation of the rotor 136 rotates and releases the plunger 144 to pressurize the fluid within the reservoir 160. Additionally, the rotation of the rotor 136 releases the drive spring 148 from the drive spring holder 260, thereby driving the microneedles 152 to extend outside of the infusion device 100. The single multi-function/step process also includes movement of the valve 168 from the pre-activated position to the activated position due to the activator button 128 engaging and moving the valve 168 when the activator button 128 is depressed, thereby commencing fluid flow between the reservoir and the microneedles 152 via the channel 172.

As noted above, the patch-like infusion device 100 also includes a safety mechanism 108. To prevent inadvertent or accidental needle stick injuries, prevent intentional re-use of the device, and to shield exposed needles, the locking needle safety mechanism 108 is provided. The safety mechanism 108 automatically activates immediately upon removal of the infusion device 100 from the skin surface of the patient. According to one embodiment described in greater detail below, a flexible adhesive pad 264 adheres to a bottom portion of the bottom enclosure 104 and a bottom portion of the safety mechanism 108. The adhesive pad 264 contacts with the patient's skin and holds the infusion device 100 in position on the skin surface during use. As shown, for example, in FIGS. 11 and 12, upon removal of the infusion device 100 from the skin surface, the safety mechanism 108 extends to a position shielding the microneedles 152. When fully extended, safety mechanism 108 locks into place and prevents accidental injury or exposure to the patient needles 152.

In general, a passive safety system is most desirable. This allows the device to be self-protecting in case of accidental removal or if the patient forgets that there is a safety step. Because one typical use for this infusion device 100 is to provide human growth hormone, which is usually given in the evening, it can be expected that patients that wear the device (such as children) may actually wear them overnight, even though the delivery may be expected to take less than 10 minutes. Without a passive system, if the infusion device 100 falls off, the microneedles 152 could re-stick the patient or a caregiver. The solution is to either limit the activities during use, or include a passive safety system.

With respect to safety systems, there are typically three options. A first option is to retract the needles 152 into the device. A second option is to shield the needles 152 to remove access, and a third option is to destroy the needles 152 in a way that prevents needle stick injuries. Other systems, such as active systems, utilize manual shielding and/or destruction, or manual release of safety features with an additional button push or similar action. A detailed description of passive safety embodiments of the present invention is provided below.

One safety embodiment of the present invention is a passive, fully enclosed pull-out design embodiment, such as safety mechanism 108. FIGS. 5, 10, and 12 are perspective cutaway views of the infusion device 100 that illustrate the safety mechanism 108 prior to activation, subsequent to activation, and subsequent to deployment of the safety mechanism 108, respectively.

Figure 13:
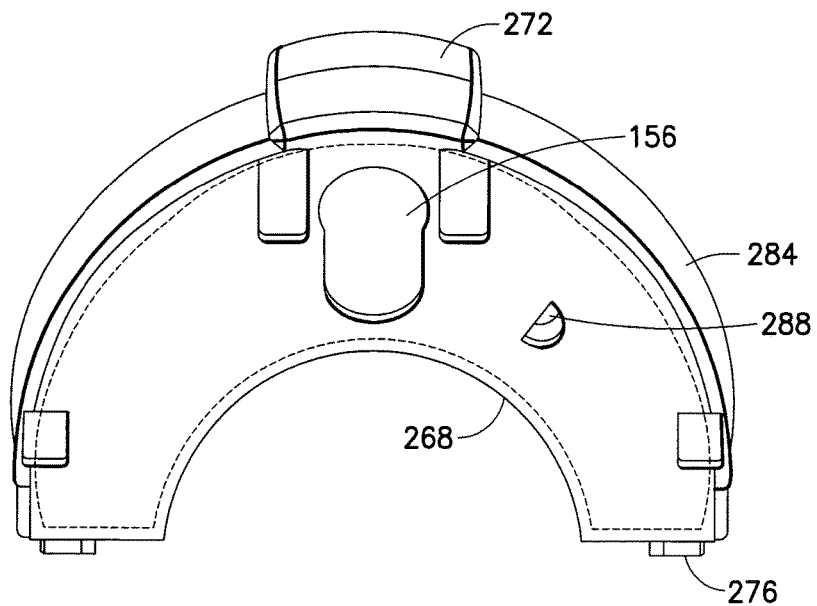
FIG. 13 illustrates a bottom surface of the safety mechanism.

When the infusion device 100 is removed from the skin, the flexible adhesive pad 264 (attached to both the bottom surface of the bottom enclosure 104 and the bottom surface of the safety mechanism 108) will pull the safety mechanism 108 out and lock it into place before the adhesive pad 264 releases the skin surface. In other words, the force required to remove the adhesive pad from the skin surface is greater than that required to deploy the safety mechanism 108. According to one embodiment, the safety mechanism 108, as shown, for example, in FIG. 13, includes a flat surface portion 268 that is in contact with the patient's skin. The flat surface 268 is where a portion of adhesive pad 264 (shown as a dotted line in FIG. 13) is affixed to safety mechanism 108 such that when the infusion device 100 is removed by the patient from the skin, the adhesive pad 264 will act to deploy the safety mechanism 108 from the infusion device 100, thereby shielding the microneedles 152, which otherwise would be exposed upon removal of the infusion device 100 from the patient. When the safety mechanism 108 is fully extended, the safety mechanism 108 locks into place and prevents accidental injury or exposure to the microneedles 152.

According to one embodiment, the adhesive pad 264 is provided in substantially two parts, one on the bulk of the bottom surface of the bottom enclosure 104, and one on the bottom surface of the safety mechanism 108. When the infusion device 100 is removed, the two patches move independently and the safety mechanism 108 is rotatable with respect to the bottom enclosure 104. According to another embodiment, the two parts are formed as a unitary, flexible adhesive pad 264 with one part being disposed on the on the bulk of the bottom surface of the bottom enclosure 104, and one part disposed on the bottom surface of the safety mechanism 108.

Figure 14:
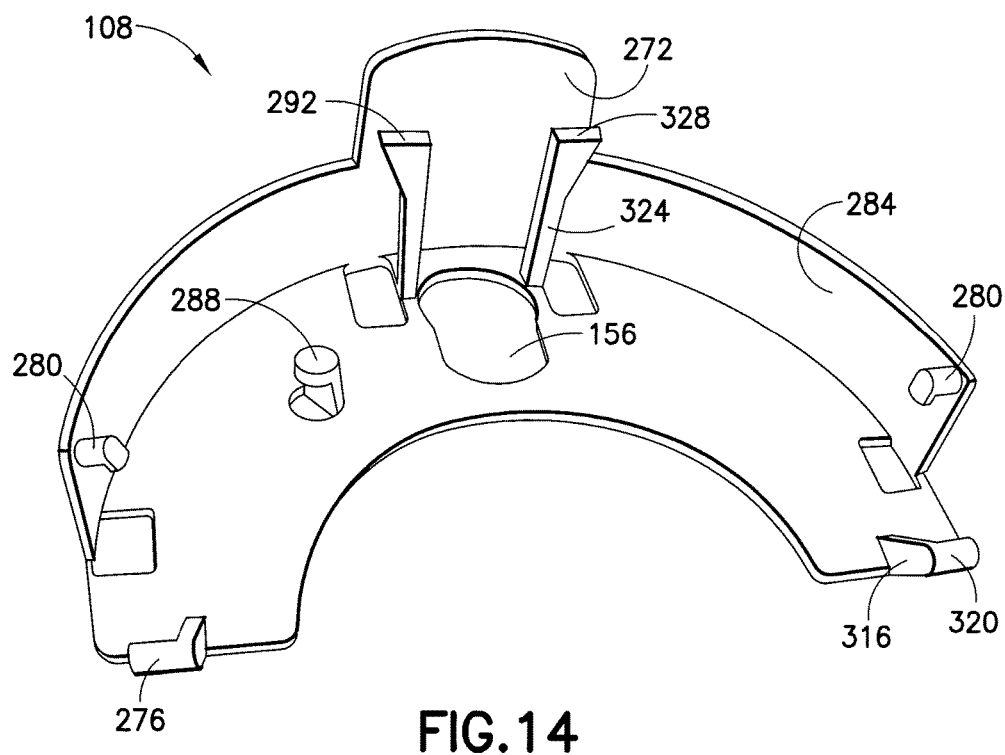
FIG. 14 further illustrates the structure of the safety mechanism.

According to one embodiment, the safety mechanism 108 is a stamped metal part. According to another embodiment, the safety mechanism 108 is made of substantially the same material as the bottom enclosure 104. As shown in FIG. 14, the safety mechanism 108 includes a front shield 272, a pair of insertion tabs 276 disposed at a rear portion of the safety mechanism 108, a pair of pivot tabs 280 disposed, respectively, at upper rear ends of a rim portion 284 of the safety mechanism 108, a guide post 288 extending upwardly from a substantially flat bottom inner surface of the safety mechanism 108, and locking posts 292 also extending upwardly from the bottom inner surface of the safety mechanism 108. Front shield 272 extends above the rim portion 284 to shield the patient from the microneedles 152 when the safety mechanism 108 is deployed. The guide post 288 includes a cutout therein to engage a safety retaining projection 296 of the rotor 136 (shown, for example, in FIGS. 7 and 9) when the rotor 136 is in the pre-activated position, to prevent the safety mechanism 108 from deploying prior to activation of the infusion device 100.

Additionally, as noted above, the safety mechanism 108 includes the needle opening 156. Prior to deployment of the safety mechanism 108, the needle opening 156 at least partially overlaps the opening 300 in bottom enclosure 104 to provide space for movement of the microneedles 152. The locking posts 292 are respectively disposed adjacent to front side edges of the needle opening 156. The bottom enclosure 104 includes a guidepost opening 304 (shown, for example, in FIGS. 7 and 9), a pair of insertion tab openings 308 (one of which is shown, for example, in FIG. 4) disposed adjacent to opposing side edges of the bottom enclosure 104, and a pair of pivot rests 312 disposed on opposing sides of the bottom enclosure 104 (shown, for example, in FIGS. 7 and 9).

Referring again to FIG. 14, insertion tabs 276 each include a connecting portion 316 and an extending portion 320. According to one embodiment, the connecting portions 316 extend from the bottom inner surface of the safety mechanism 108 toward a rear of the infusion device 100 at a non-perpendicular angle with respect to the bottom inner surface of the safety mechanism 108. Extending portions 320 each extend substantially perpendicularly from the extending portions 320 toward respective outer sides of the safety mechanism 108. To assemble the safety mechanism 108 to the bottom enclosure 104, safety mechanism 108 is held at an approximately 45° angle with respect to the bottom enclosure 104 and the insertion tabs 276 are inserted through the insertion tab openings 308. The safety mechanism 108 is then rotated to a position such that the guidepost 288 is inserted through the guidepost opening 304 and the bottom inner surface of the safety mechanism 108 is substantially parallel and in contact with the bottom surface of the bottom enclosure 104.

Referring again to FIGS. 7 and 9, although these views illustrate the rotor 136 in the activated position, the exploded nature of FIGS. 7 and 9 is convenient to illustrate this stage of the assembly of the safety mechanism 108 to the bottom enclosure 104. It will be understood, however, that the safety mechanism 108 should be assembled to the bottom enclosure prior to activation. Subsequent to the upward rotation of the safety mechanism 108, as shown in FIG. 4, safety mechanism 108 translates rearward with respect to the bottom enclosure 104 such that pivot tabs 280 clear respective front edges of the pivot rests 312 and are disposed above the pivot rests 312, the locking posts 292 are disposed adjacent to side edges of the opening 300 of the bottom enclosure 104, and the safety retaining projection 296 of the rotor 136 engages the guide post 288.

Returning to FIG. 14, each of the locking posts 292 includes a post extending portion 324 extending substantially perpendicular from the flat bottom inner surface of the safety mechanism 108, and a wedge portion 328 disposed at an end of the post extending portion 324. As a height of the wedge portion 328 increases with respect to the bottom inner surface of the safety mechanism 108, a width of the wedge portion 328 increases.

As the safety mechanism 108 deploys and rotates downward with respect to the bottom enclosure 104, the wedge portions 328 act against respective side edges of the openings 180 of the bottom enclosure 104, causing the locking posts 192 to deform elastically toward one another. As the safety mechanism 108 is fully deployed, the tabs 280 become seated in pivot rests 312. Additionally, top edges of the wedge portions 328 pass bottom edges of the opening 300 and the locking posts 292 snap back to their substantially un-deformed states, providing an audible click and tactile feedback communicating that the safety mechanism 108 is fully deployed, and therefore, that the microneedles 152 are covered. Returning to FIGS. 11 and 12, once the safety mechanism 108 is fully deployed and the locking posts 292 have snapped back to their substantially un-deformed states, the top edges of the wedge portions 328 engage the bottom surface of the bottom enclosure 104 adjacent to the opening 300, thereby preventing the safety mechanism 108 from rotating upward with respect to the bottom enclosure 104 and exposing the microneedles 152. Additionally, as noted above, front shield 272 shields the patient from the microneedles 152.

Accordingly, the safety mechanism 108 is a passive safety embodiment provided as a single part and provides a good lock that will not crush under human loads. With this passive safety mechanism, no additional forces are applied to the skin during injection, and the microneedles 152 are safely held within the infusion device 100 after use.

After use of the infusion device 100, the patient can once again inspect the device to ensure the entire dose was delivered. In this regard, as shown in FIGS. 15A-D, the infusion device 100 includes the end-of-dose indicator (EDI) 124. The EDI 124 includes a main body 332 and first and second arms 336 and 340 extending substantially horizontally with respect to a top of the main body 332.

The EDI 124 also includes a spring arm 344 that curves upwardly from the top of the main body 332. According to one embodiment, the spring arm 344 pushes against a bottom side of the reservoir subassembly 120, elastically biasing the EDI 124 toward the bottom enclosure 104, to ensure that the EDI 124 does not move freely out of the infusion device 100, for example, during shipping and handling of the infusion device 100.

Returning to FIG. 4, the main body 332 is disposed in an EDI channel 348 and translates substantially vertically therein. The EDI channel adjacent to one of the recessed channels 204 that guides legs 208 and feet 212 of plunger 144. The first arm 336 extends across a top of this recessed channel 204.

Returning to FIG. 15A, a vertical extrusion 352 extends upwardly from an end of the second arm 340. When the reservoir contents have been delivered, the vertical extrusion extends through an EDI opening 356 (see, for example, FIG. 15C) in the top enclosure 116 to communicate that the end of the dose has been reached. According to one embodiment, the EDI 124 is formed as a one-piece construction.

Figure 15A:
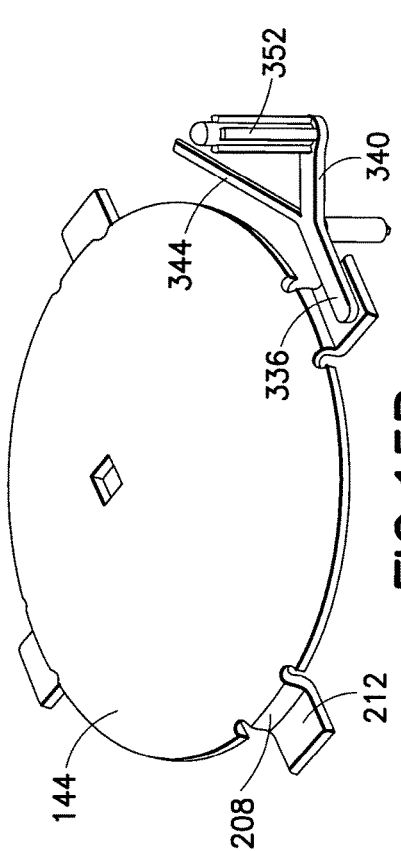
FIGS. 15A-15D illustrate an end-of-dose indicator and the operation thereof in the infusion device of FIG. 1.
Figure 15B:
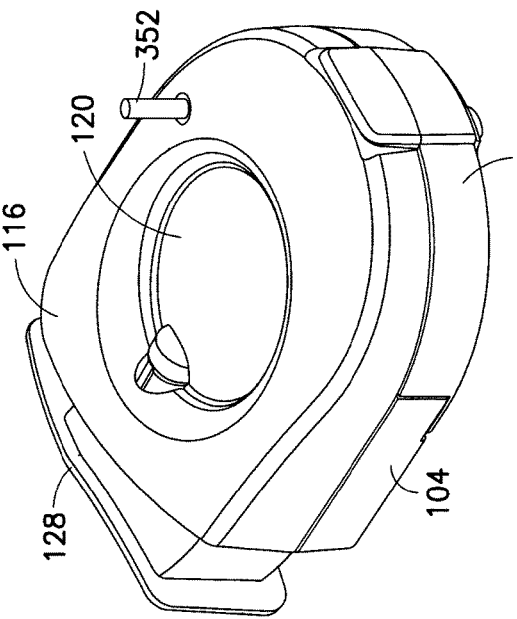
Figure 15C:
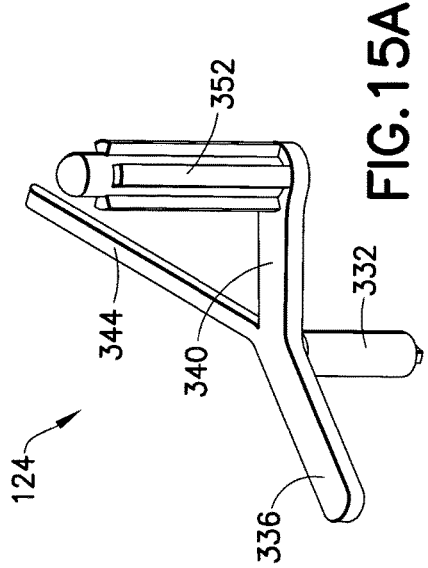
Figure 15D:
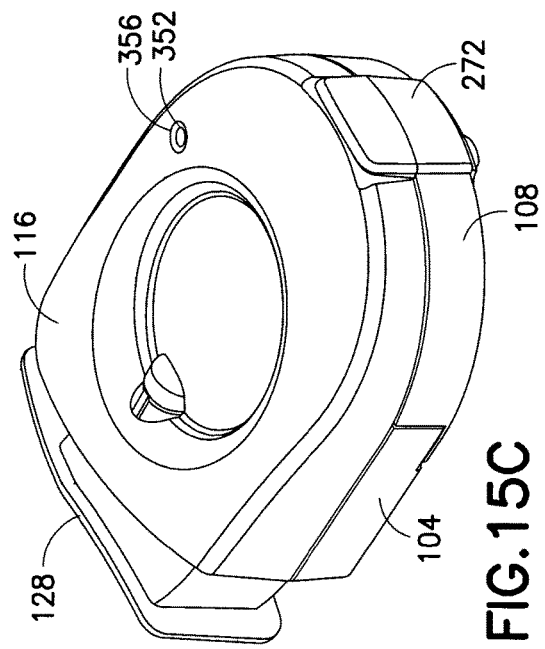

As shown in FIG. 15B, as the plunger 144 travels upwardly in the cylindrical housing 200 due to the pressurization spring 140 subsequent to activation, one of the feet 212 of the plunger 144 contacts the first arm of the EDI 124. The foot 212 lifts the EDI 124 upward, overcoming the bias of the spring arm 344, and causing the vertical extrusion 352 to increasingly extend through the EDI opening 356 during delivery of the reservoir contents. Referring back to FIG. 10, vertical extrusion 352 partially extends from the infusion device 100. Once the delivery of the reservoir contents is complete and the plunger has achieved its full stroke, the vertical extrusion 352 is fully extended, as shown in FIG. 15D. Thus, the EDI 124 employs the linear movement of the plunger 144 to generate linear movement of the EDI 124 that is visible outside of the infusion device 100 thereby communicating the delivery of the reservoir contents.

Figure 16:
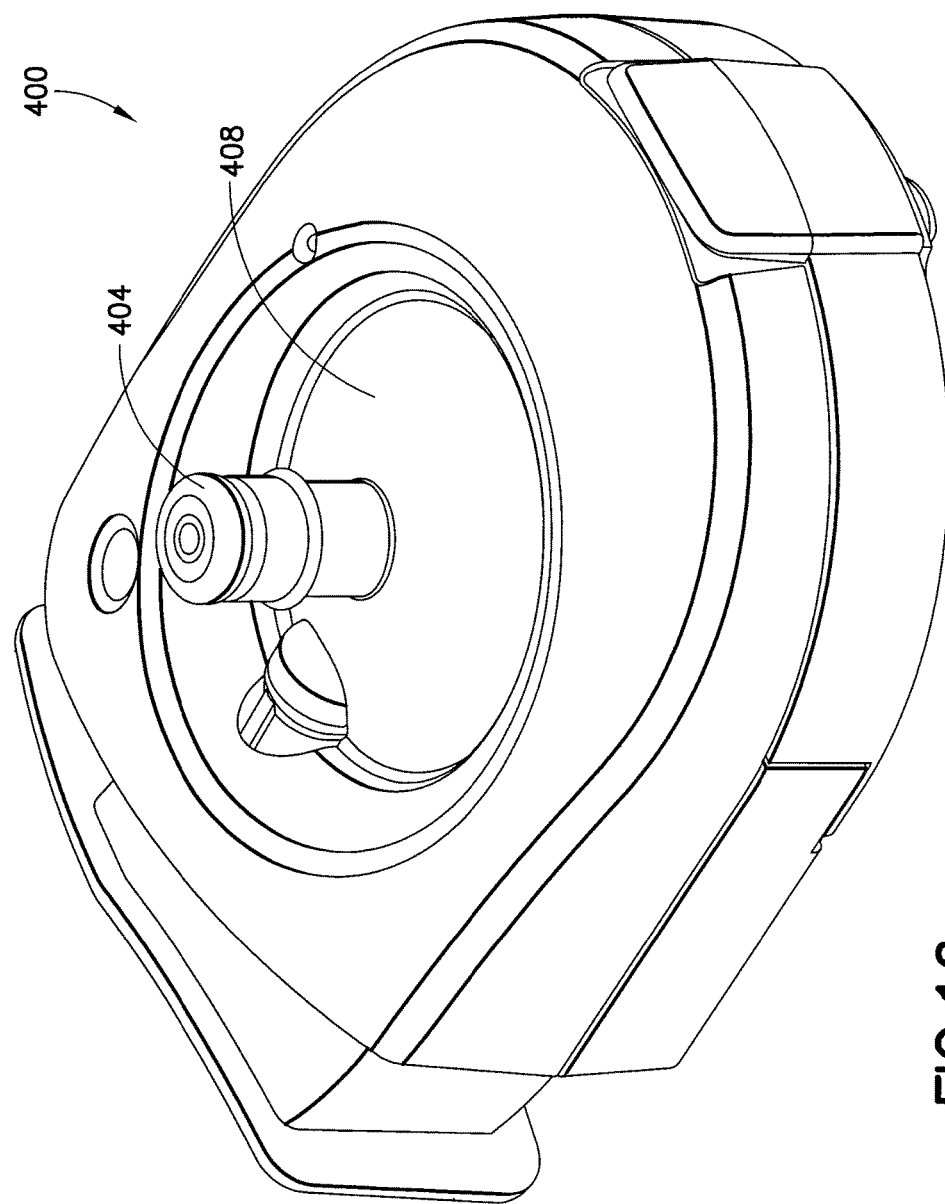
FIG. 16 illustrates an embodiment of an infusion device with an injection port.

FIG. 16 illustrates an embodiment of an infusion device 400 with an injection port 404. The injection port provides access to an evacuated or partially-filled reservoir 408, so that the patient can inject a substance or combination of substances into the reservoir prior to activation. Alternatively, a pharmaceutical manufacturer or pharmacist could employ the injection port 404 to fill the infusion device 400 with a substance or combination of substances prior to sale. In substantially all other respects, the infusion device 400 is similar to the previously-described infusion device 100.

Operation of the infusion device 100 will now be described. The embodiments of the present invention described above preferably include a push-button (activator button 128) design wherein the infusion device 100 can be positioned and affixed to a skin surface, and energized and/or activated by pressing the activator button 128. More specifically, in a first step, the patient removes the device from a sterile packaging (not shown), and removes a release liner (discussed in greater detail below) of the adhesive pad 264. The patient also removes the needle cover 114 (also discussed in greater detail below). Upon removal of the infusion device 100 from the package and prior to use (see, for example, FIGS. 1, 2, 4, and 5), the infusion device 100 in the pre-activated state allows the patient to inspect both the device and the contents therein, including inspection for missing or damaged components, expiration dates(s), hazy or color-shifted drugs, and so forth.

The next step is the positioning and application of the infusion device 100 to the patient's skin surface. Like a medicinal patch, the patient firmly presses the infusion device 100 onto the skin. One side of the adhesive pad 264 adheres to a bottom surface of the bottom enclosure 104 and a bottom surface of the safety mechanism 108, and the opposing side of the adhesive pad 264 secures the infusion device 100 to the skin of the patient. In an alternative embodiment, the adhesive pad 264 may be replaced by an adhesive applied directly to the bottom surface of the bottom enclosure 104 and the bottom surface of the safety mechanism 108. Such an adhesive would be covered by the release liner prior to use of the infusion device 100. These bottom surfaces (of the bottom enclosure 104 and the safety mechanism 108) can be flat, contoured, or shaped in any suitable fashion and the adhesive pad 264 is secured thereon. As discussed in greater detail below, according to one embodiment, prior to shipping, the release liner, such as a film, is applied to the patient-side of the adhesive pad 264 to preserve the adhesive during shipping. As noted above, prior to use, the patient peels back the release liner, thereby exposing the adhesive pad 264 (or adhesive) for placement against the skin.

After removing the release liner, the patient is able to place the infusion device 100 against the skin and press to ensure proper adhesion. As noted above, once properly positioned, the device is activated by depressing the activator button 128. This activation step releases plunger 144 and the pressurization spring 140, allowing a plunger 144 to press against the flexible film (reservoir dome seal 164) of the reservoir 160, thereby pressurizing the reservoir. This activation step also serves to release the drive spring 148 from the drive spring holder 260 of the rotor 136, thereby driving the microneedles 152 to extend outside the infusion device 100 (through the opening 300 in the bottom enclosure 104 and the needle opening 156 of the safety mechanism 108) and seat the microneedles 152 within the patient. Further, the activation step opens the valve 168, establishing a fluid communication path between the reservoir 160 and the microneedles 152, via the channel 172 (see, for example, FIGS. 8-10). A significant benefit derives from the ability to achieve each of these actions in a single push-button operation. Additionally, another significant benefit includes the use of a continuous fluid communication path comprised entirely within the reservoir subassembly 120.

Once activated, the patient typically leaves the infusion device 100 in position, or wears the device, for some period of time (such as ten minutes to seventy-two hours) for complete delivery of the reservoir contents. The patient then removes and discards the device with no damage to the underlying skin or tissue. Upon intentional or accidental removal, one or more safety features deploy to shield the exposed microneedles 152. More specifically, when the infusion device 100 is removed by the patient from the skin, the adhesive pad 264 acts to deploy the safety mechanism 108 from the infusion device 100, thereby shielding the microneedles 152, which otherwise would be exposed upon removal of the infusion device 100 from the patient. When the safety mechanism 108 is fully extended, the safety mechanism 108 locks into place and prevents accidental injury or exposure to the microneedles 152. The safety features, however, can be configured to not deploy if the activator button 128 has not been depressed and the microneedles 152 have not been extended, thereby preventing pre-use safety mechanism deployment. After use, the patient can once again inspect the device to ensure the entire dose was delivered. For example, the patient can view the reservoir interior through the transparent dome 176 and/or inspect the EDI 124.

The described embodiments are suitable for use in administering various substances, including medications and pharmaceutical agents, to a patient, and particularly to a human patient. As used herein, a pharmaceutical agent includes a substance having biological activity that can be delivered through the body membranes and surfaces, and particularly the skin. Examples, listed in greater detail below, include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally or subcutaneously to a patient include human growth hormone, insulin, proteins, peptides and fragments thereof. The proteins and peptides can be naturally occurring, synthesized or recombinantly produced. Additionally, the device can be used in cell therapy, as during intradermal infusion of dendritic cells. Still other substances which can be delivered in accordance with the method of the present invention can be selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atherosclerosis malaria, *E. coli*, Alzheimers, *H. pylori, salmonella*, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents as described in U.S. Pat. No. 6,569,143, entitled "Method of Intradermally Injecting Substances", the entire content of which is expressly incorporated herein by reference.

Vaccine formulations which can be delivered in accordance with the system and method of the present invention can be selected from the group consisting of an antigen or antigenic composition capable of eliciting an immune response against a human pathogen, which antigen or antigenic composition is derived from HIV-1, (such as tat, nef, gp120 or gp160), human herpes viruses (HSV), such as gD or derivatives thereof or Immediate Early protein such as ICP27 from HSVI or HSV2, cytomegalovirus (CMV (esp Human) (such as gB or derivatives thereof), Rotavirus (including live-attenuated viruses), Epstein Barr virus (such as gp350 or derivatives thereof), Varicella Zoster Virus (VZV, such as gpl, II and IE63) or from a hepatitis virus such as hepatitis B virus (for example Hepatitis B Surface antigen or a derivative thereof), hepatitis A virus (HAV), hepatitis C virus and hepatitis E virus, or from other viral pathogens, such as paramyxoviruses: Respiratory Syncytial virus (RSV, such as F and G proteins or derivatives thereof), parainfluenza virus, measles virus, mumps virus, human papilloma viruses (HPV for example HPV6, 11, 16, 18), flaviviruses (e.g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes or purified or recombinant proteins thereof, such as HA, NP, NA, or M proteins, or combinations thereof), or derived from bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans; H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. Epidermidis; Enterococcus* spp., including *E. faecalis, E. faecium; Clostridium* spp., including *C. tetani* (for example tetanus toxin and derivative thereof), *C. botulinum* (for example Botulinum toxin and derivative thereof), *C. difficile* (for example clostridium toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. Burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. Hermsii; Ehrlichia* spp., including *E. equi* and the agent of the Human Granulocytic Ehrlichiosis; *Rickettsia* spp, including *R. rickettsii; Chlamydia* spp., including *C. Trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. Falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. Carinii; Trichomonas* spp., including *T. vaginalis; Schisostoma* spp., including *S. mansoni*, or derived from yeast such as *Candida* spp., including *C. albicans; Cryptococcus* spp., including *C. neoformans*, as described in PCT Patent Publication No. WO 02/083214, entitled "Vaccine Delivery System", the entire content of which is expressly incorporated herein by reference.

These also include other preferred specific antigens for *M. tuberculosis*, for example Tb Ra12, Tb H9, Tb Ra35, Tb38-1, Erd14, DPV, MTI, MSL, mTTC2 and hTCC1. Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI. Most preferred antigens for Chlamydia include for example the High Molecular Weight Protein (HWMP), ORF3, and putative membrane proteins (Pmps). Preferred bacterial vaccines comprise antigens derived from *Streptococcus* spp, including *S. pneumoniae* (for example capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof. Other preferred bacterial vaccines comprise antigens derived from *Haemophilus* spp., including *H. influenzae* type B ("Hib", for example PRP and conjugates thereof), non typeable *H. influenzae*, for example OMP26, high molecular weight adhesins, P5, P6, protein D and lipoprotein D, and fimbrin and fimbrin derived peptides or multiple copy variants or fusion proteins thereof. Derivatives of Hepatitis B Surface antigen are well known in the art and include, inter alia, PreS1, PreS2 S antigens. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In addition to the delivery of substances listed above, the infusion device 100 can also be used for withdrawing a substance from a patient, or monitoring a level of a substance in the patient. Examples of substances that can be monitored or withdrawn include blood, interstitial fluid or plasma. The withdrawn substances can then be analyzed for analytes, glucose, drugs, and the like.

As noted above, according to one embodiment, the infusion device 100 includes a needle cover 114 and a release liner for the adhesive pad 264. Both the needle cover 114 and the release liner are removed prior to use of the infusion device 100. Additionally, the needle cover 114 and the release liner are disposed of subsequent to removal from the infusion device 100. One solution is to combine the needle cover and the release liner such that removal of the needle cover also removes the release liner. Another solution is to combine the needle cover and the release liner such that removal of the release liner also removes the needle cover. Optionally, the needle cover and the release liner can also be disposed of simultaneously.

Figure 18:
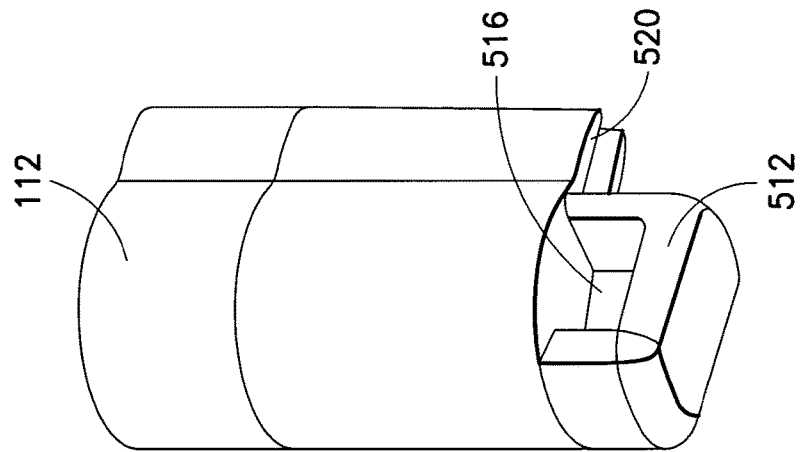
FIG. 18 illustrates a needle-covering portion of a needle cover in the infusion device of FIG. 1.
Figure 17:
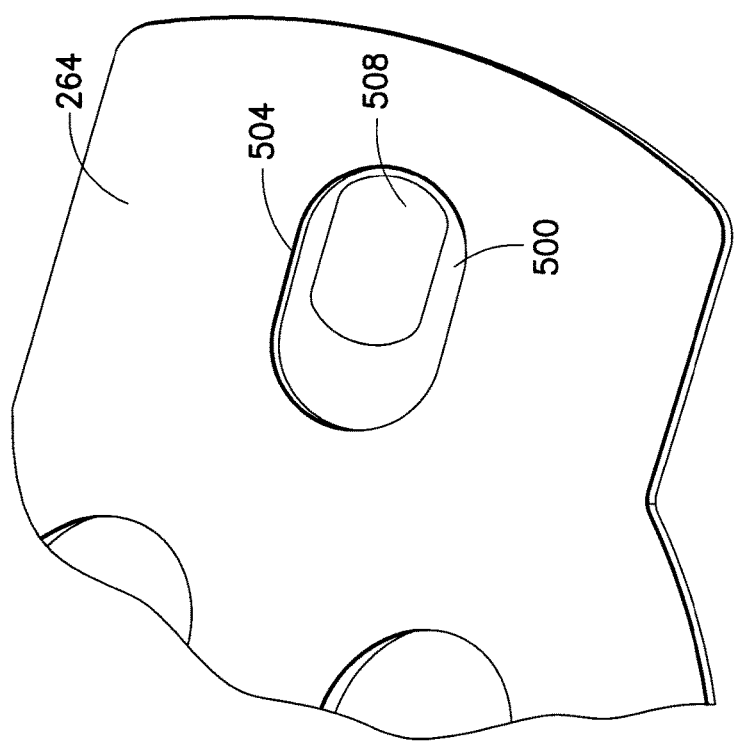
FIG. 17 illustrates an embodiment of an adhesive pad and adhesive release liner in the infusion device of FIG. 1.
Figure 19:
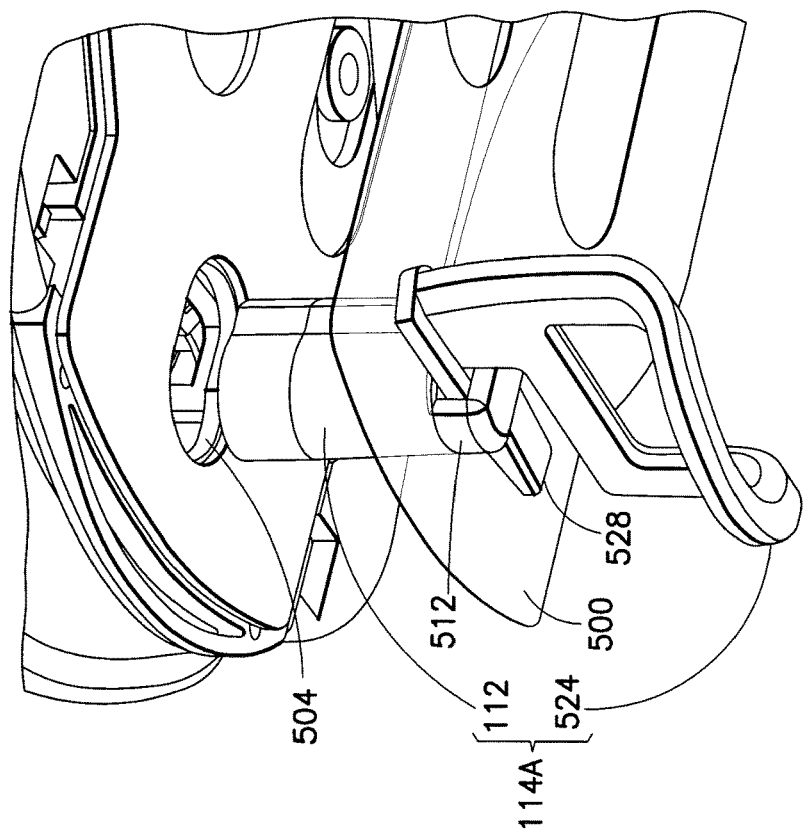
FIG. 19 illustrates an embodiment of a needle cover including the needle-covering portion of FIG. 18.

FIG. 17 illustrates an embodiment of the adhesive pad 264 and an adhesive release liner 500 of the infusion device 100, and FIG. 18 illustrates the needle-covering portion 112 of the needle cover 114. Additionally, FIG. 19 illustrates an embodiment of a combination of a needle cover 114A (including the needle-covering portion 112) and the release liner 500. As shown in FIG. 17, adhesive pad 164 includes a needle cover opening 504, and release liner 500 includes a liner opening 508. FIG. 18 illustrates that needle-covering portion 112 includes an eyelet 512 with an eyelet opening 516, and a shoulder or flange 520. As noted previously, according to one embodiment, the needle-covering portion 112 is attached to the needle manifold via a press fit. Though FIGS. 17 and 18 are not to the same scale, liner opening 508 is larger than eyelet 512 but smaller than flange 520, and thus, eyelet 512 can be inserted through liner opening 508 such that the flange 520 contacts the release liner 500. Additionally, needle cover opening 504 is larger than the cross section of needle-covering portion 112, such that the entire needle-covering portion 112 can be inserted through needle cover opening 504.

As shown in FIG. 19, needle cover 114A includes both needle-covering portion 112 and a retaining portion or pull tab portion 524. The pull tab portion 524 includes a pull tab arm 528 that is insertable into the eyelet opening 516. FIG. 19 illustrates that after the eyelet 512 has been inserted through the liner opening 508, once the pull tab arm 528 is inserted into the eyelet opening 516, the pull tab portion 524 retains the release liner 500 on the needle cover 114A. According to one embodiment, at least one of the eyelet 512 and the pull tab portion 524 is sufficiently flexible such that subsequent to the insertion of the pull tab arm 528 into the eyelet opening 516, the pull tab portion 524 can be rotated approximately 90° from the position illustrated in FIG. 19, for example, to minimize an external size or profile of the infusion device 100 for packaging. Additionally, though pull tab portion 524 can be rotated either forward or backward, rotation of the pull tab portion 524 toward the activator button 128 (similar to the embodiment illustrated in FIG. 20B) more effectively reduces the external profile of the infusion device 100.

To install the embodiment illustrated in FIG. 19, the needle-covering portion 112 is inserted through the needle opening 156 and attached to the needle manifold via a press fit, such that eyelet 512 extends outside of the infusion device 100. Subsequently, the adhesive pad 264 is adhered to the bottom enclosure 104 and the safety mechanism 108 such that needle cover opening 504 of the adhesive pad 264 corresponds substantially to the needle opening 156. Additionally, the release liner 500 is adhered to the adhesive pad 264 such that the eyelet 512 is inserted through the liner opening 508 and the release liner 500 contacts the flange 520. It will be understood that the adhesive pad 264 and the release liner 500 may be applied in a single operation. Next, the pull tab arm 528 is inserted through the eyelet opening 516, thereby securing the release liner 500, and combining the release liner 500 and the needle cover 114A.

To remove the release liner 500 and the needle cover 114A, the patient grasps and pulls the pull tab portion 524. Because the release liner 500 is retained between the pull tab portion 524 and the flange 520, such a single action by the patient not only removes the needle cover 114 from the needle manifold, but also removes the release liner 500 from the adhesive pad 264. Additionally, because the release liner 500 remains retained between the pull tab portion 524 and the flange 520 subsequent to removal from the infusion device 100, the patient can easily dispose of the combined release liner 500 and needle cover 114A.

Figure 20A:
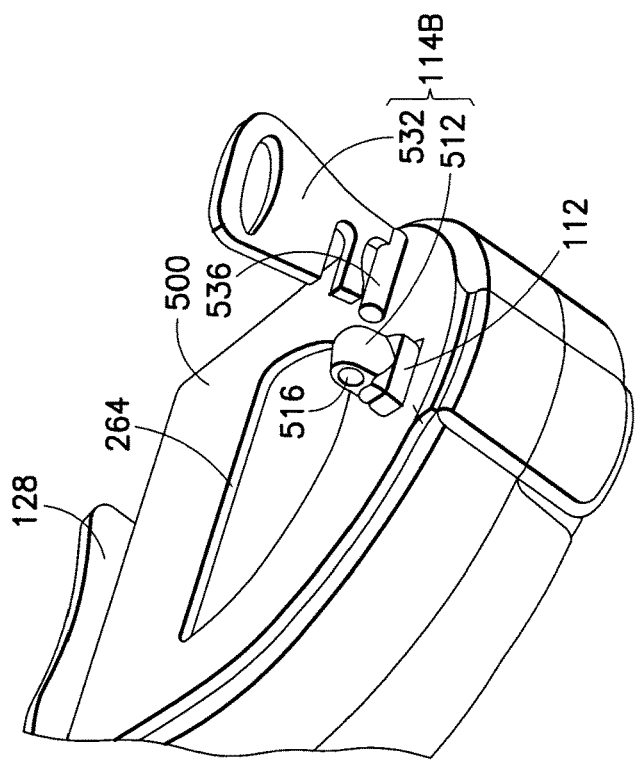
FIGS. 20A to 20C illustrate an embodiment of a needle cover in the infusion device of FIG. 1 including the needle-covering portion of FIG. 18.
Figure 20C:
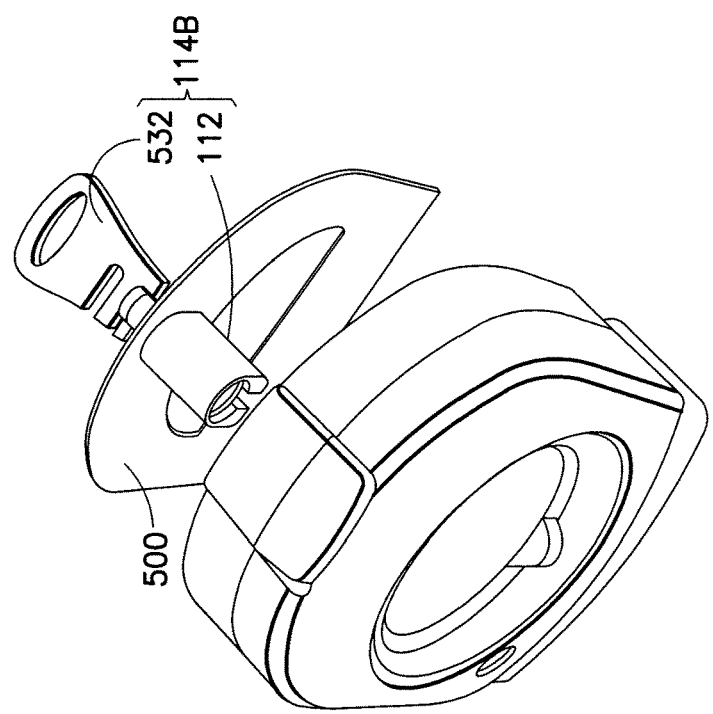
Figure 20B:
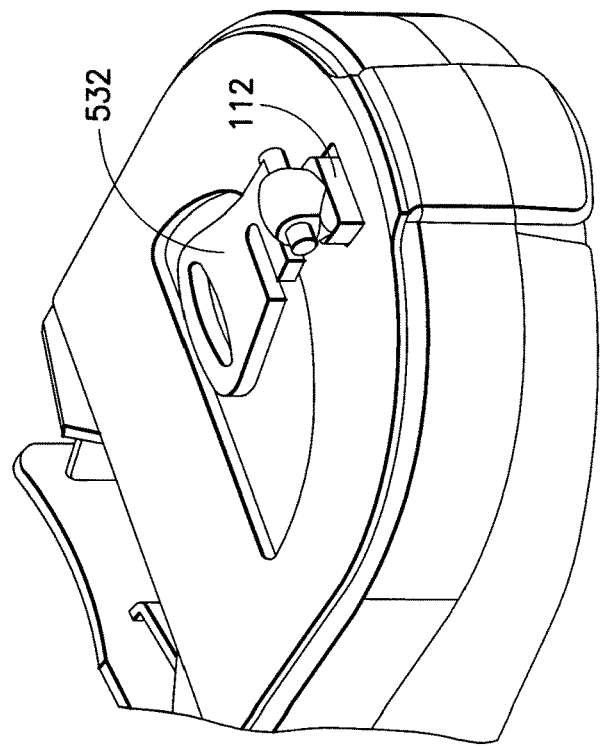

Similar to the embodiment of FIG. 19, FIGS. 20A-20C illustrates an embodiment of a needle cover 114B. In this embodiment, as shown in FIG. 20A, the pull tab portion 532 and has a pull tab arm 536 that is inserted into the eyelet opening 516 of the eyelet 512 subsequent to installation of the adhesive pad 264 and the release liner 500. In contrast to the embodiment of FIG. 19, however, the pull tab portion 532 is substantially planar. As shown in FIG. 20B, such a planar configuration provides for a further-reduced profile in comparison to the embodiment of FIG. 19, thereby requiring a smaller envelope for packaging. Additionally, during assembly, the configuration of the pull tab portion 532 as shown in FIG. 20B may reduce side stresses to the needle cover 114B that may contribute to compromising a seal between the needle-covering portion 112 and the needle manifold.

Further, according to one embodiment, the pull tab arm 536 includes indexing to help align the pull tab portion 532 in a first position substantially aligned with the needle-covering portion 112 and a second position substantially parallel to a bottom surface of the bottom enclosure 104. FIG. 20C illustrates the combined release liner 500 and needle cover 114B subsequent to removal from the infusion device 100 and ready for disposal.

Figure 21B:
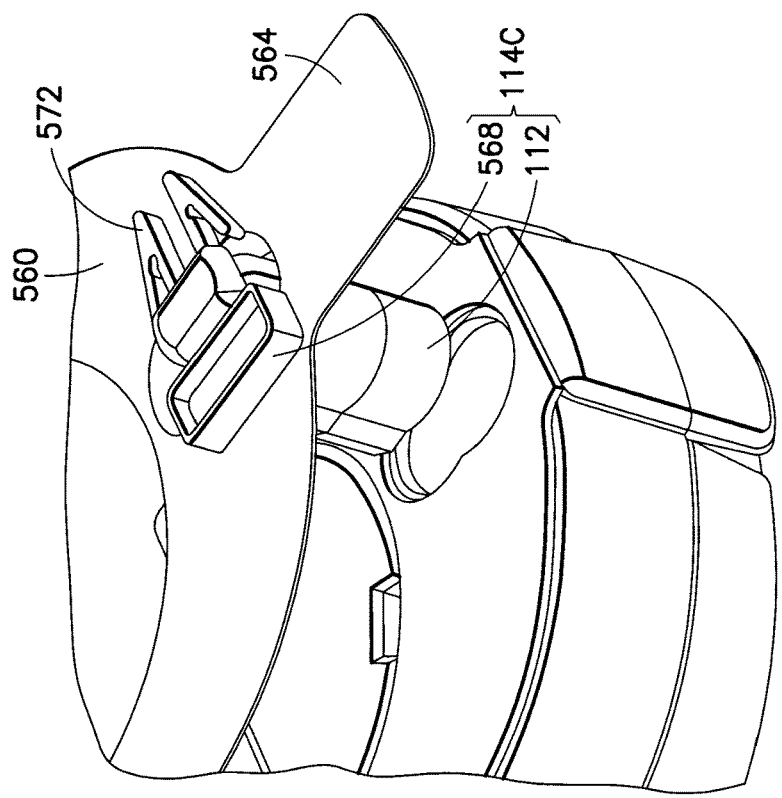
FIGS. 21A and 21B illustrate an embodiment of a needle cover in the infusion device of FIG. 1 including the needle-covering portion of FIG. 18.
Figure 21A:
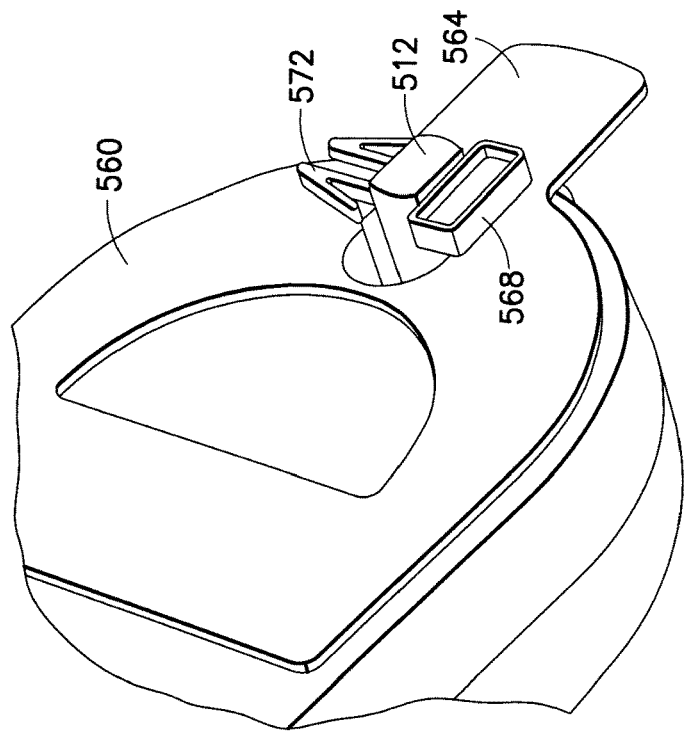

FIGS. 21A and 21B illustrate another embodiment of a needle cover 114C and a release liner 560. The release liner 560 includes a pull tab 564. Additionally, the needle cover 114C includes the needle-covering portion 112 and a snap clip portion 568. The snap clip portion 568 includes a pair of cantilevered snap clip wings 572. Each of the snap clip wings 572 is elastically deformable and has a sloped face, such that as the snap clip portion 568 is inserted into the eyelet opening 516, the sloped faces engage the eyelet 512 and the contact therebetween progressively deforms the snap clip wings 572. After trailing edges of the sloped faces pass through the eyelet opening 516, the snap clip wings 572 substantially return to their respective undeformed positions, thereby locking the snap clip portion 568 in the eyelet 512, and retaining the release liner 560 between the snap clip portion 568 and the flange 520.

To remove the combined release liner 560 and needle cover 114C, the patient grasps and pulls the pull tab 564 of the release liner 560. Because the release liner 560 is retained between the snap clip portion 568 and the flange 520, such a single action removes both the release liner 560 and the needle cover 114C from the infusion device 100. FIG. 21B illustrates the combined release liner 560 and needle cover 114C subsequent to removal from the infusion device 100 and ready for disposal.

In contrast to FIGS. 18, 19, 20A-20C, 21A and 21B, in each of the needle covers illustrated in FIGS. 22A-22D, 23A, 23B, 24, 25A, and 25B, a needle-covering portion and a pull tab portion are integrally formed as a unitary structure. For example, FIGS. 22A-22D illustrate a needle cover 114D that includes a needle-covering portion 112D and a pull tab portion 580 that are connected by a living hinge, and are thus, integrally formed as a unitary structure. A living hinge can be provided as a thin flexible portion of plastic joining two more rigid plastic parts together, allowing the more rigid portions to rotate with respect to each other along, such that the living hinge is an axis of rotation. In other words, the thin web of the living hinge provides for rotation between the members connected by the living hinge. As shown, for example in FIGS. 22B and 22C, the living hinge permits the pull tab portion 580 to move between a first position substantially aligned with the needle-covering portion 112D (FIG. 22B) and a second position (FIG. 22C) approximately 90° from the first position. In the second position, the needle cover 114D provide a smaller profile and permits a smaller envelope for packaging. Additionally, because of the smaller profile and configuration in the second position, the needle cover 114D is less likely to receive accidental impacts during assembly, and thus reduces side stresses to the needle cover 114D that may contribute to compromising a seal between the needle-covering portion 112D and the needle manifold.

Figure 22B:
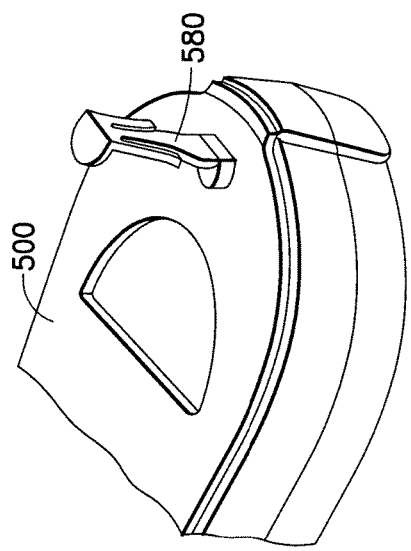
FIGS. 22A-22D illustrate an embodiment of a needle cover in the infusion device of FIG. 1.
Figure 22D:
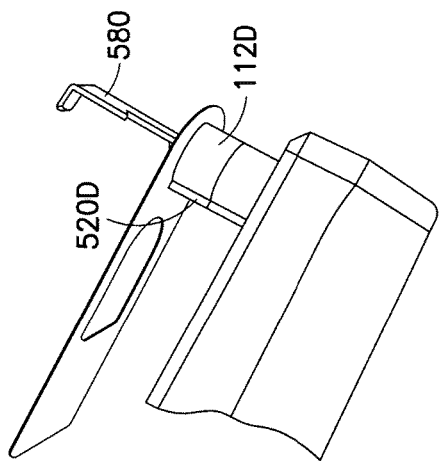
Figure 22A:
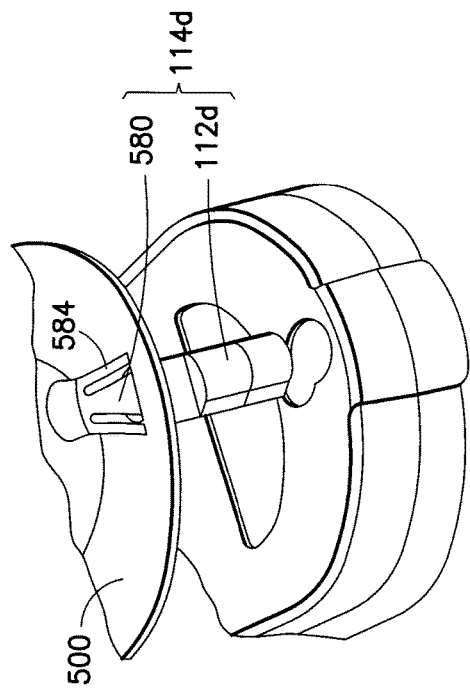
Figure 22C:
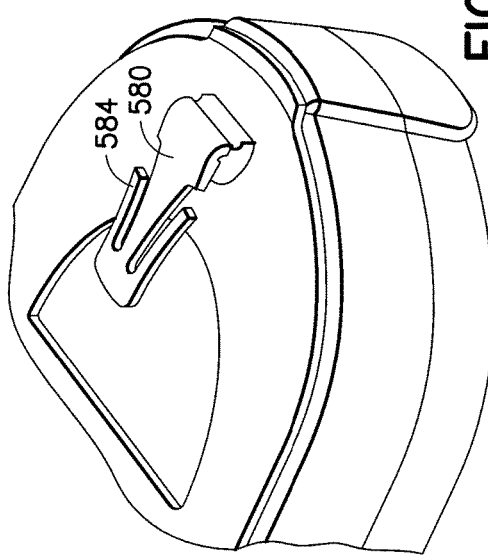

As shown in FIG. 22A, the pull tab portion 580 includes a pair of cantilevered pull tab wings 584. Each of the pull tab wings 584 is elastically deformable and has a sloped face, such that as the pull tab portion 580 is inserted into the liner opening 508, the sloped faces engage the release liner 500 and the contact therebetween progressively deforms the pull tab wings 584. After trailing edges of the sloped faces pass through the liner opening 508, the pull tab wings 584 substantially return to their respective undeformed positions, thereby locking the release liner onto the needle cover 114D, and retaining the release liner 500 between the pull tab wings 584 and the flange 520D (see, for example, FIGS. 22A and 22D).

To remove the combined release liner 500 and needle cover 114D, the patient rotates the pull tab portion 580 from the second position to the first position such that the pull tab portion 580 is substantially aligned with the needle-covering portion 112D. Then, the patient grasps and pulls the pull tab portion 580. Because the release liner 500 is retained between the pull tab wings 584 and the flange 520D, such a single action removes both the release liner 500 and the needle cover 114D from the infusion device 100. FIG. 22A illustrates the combined release liner 500 and needle cover 114D during removal from the infusion device 100. Subsequently, the combined release liner 500 and the needle cover 114D are ready for disposal.

Figure 23B:
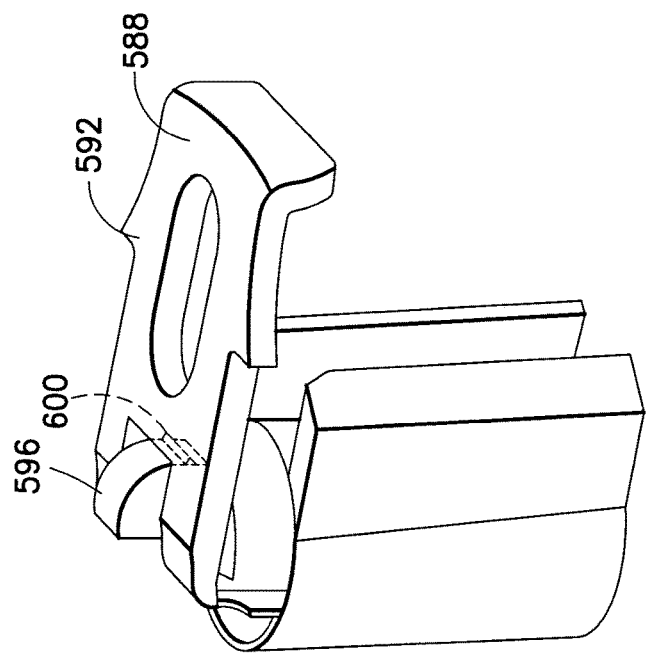
FIGS. 23A and 23B illustrate an embodiment of a needle cover in the infusion device of FIG. 1.
Figure 23A:
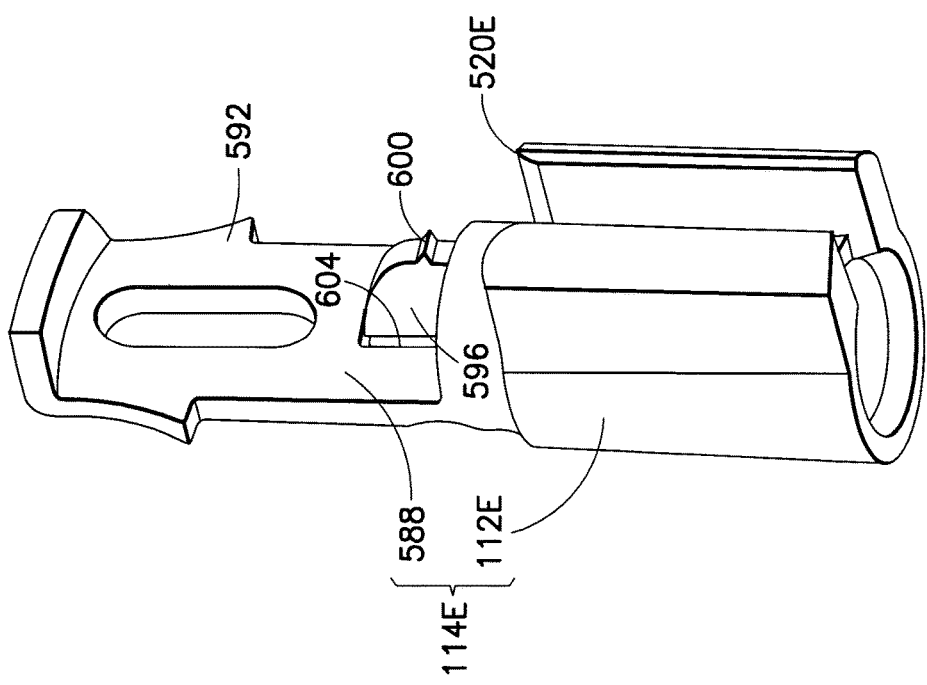

FIGS. 23A and 23B and illustrate yet another embodiment of a needle cover 114E that is combinable with the release liner 500. The needle cover 114E includes a needle-covering portion 112E and a pull tab portion 588, which includes a pair of pull tab hooks 592. At least one of the release liner 500 and the pair of pull tab hooks 592 is sufficiently elastically deformable that the pull tab hooks 592 are insertable through the liner opening 508. Subsequent to such an insertion, the release liner 500 is retained on the needle cover 114E between the flange 520E and the pull tab hooks 592.

In addition to the flange 520E, the needle-covering portion 112E also includes a post 596 extending therefrom, which has a post hook 600, as shown in FIG. 23A. Corresponding to the post 596, the pull tab portion 588 includes a slot 604. According to one embodiment, the needle cover 114E is integrally formed as a unitary structure, and the pull tab portion 588 is connected to the needle-covering portion 112E by a living hinge.

When the pull tab portion 588 is rotated from a first position (FIG. 23A) substantially aligned with a main or longitudinal axis of the needle-covering portion 112E to a second position (FIG. 23B) approximately 90° from the first position, the post hook 600 engages an edge of the slot 600 for to maintain or lock the pull tab portion 588 and the second position. When installed on the infusion device 100, the pull tab portion 588 of the needle cover 114E being configured in the second position provides a small profile, and thus allows for a small envelope for packaging the infusion device 100. Additionally, during assembly, the needle cover 114E being configured in the second position may reduce side stresses to the needle cover 114E that may contribute to compromising a seal between the needle-covering portion 112E and the needle manifold.

To remove the combined release liner 500 and needle cover 114E from the infusion device 100, the patient first applies sufficient force to disengage the edge of the slot 604 from the post hook 600 and rotates the pull tab portion 588 from the second position to the first position such that the pull tab portion 588 is substantially aligned with the needle-covering portion 112E. Then, the patient grasps and pulls the pull tab portion 588. Because the release liner 500 is retained between the pull tab hooks 592 and the flange 520E, such a single action removes both the release liner 500 and the needle cover 114E from the infusion device 100. Subsequently, the combined release liner 500 and the needle cover 114E are ready for disposal.

Figure 24:
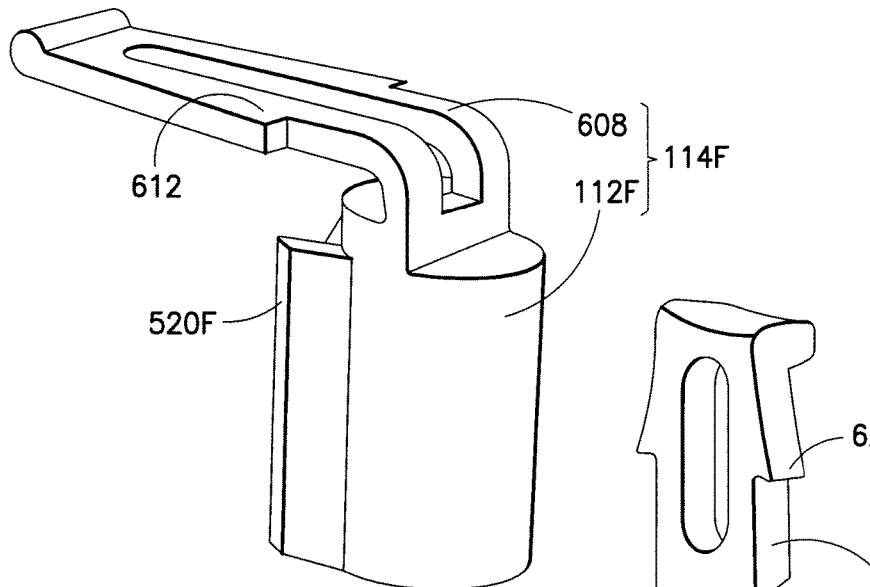
FIG. 24 illustrates an embodiment of a needle cover in the infusion device of FIG. 1.

FIG. 24 illustrates still yet another embodiment of a needle cover 114F that is combinable with the release liner 500. The needle cover 114F includes a needle-covering portion 112F and a pull tab portion 608, which includes a pair of pull tab hooks 612. At least one of the release liner 500 and the pair of pull tab hooks 612 is sufficiently elastically deformable that the pull tab hooks 612 are insertable through the liner opening 508. Subsequent to such an insertion, the release liner 500 is retained on the needle cover 114F between the flange 520F and the pull tab hooks 612.

According to one embodiment, the needle cover 114F is integrally formed as a unitary structure. As shown in FIG. 24, a main or longitudinal axis of the pull tab portion 608 forms an approximately 90° angle with respect to a main or longitudinal axis of the needle-covering portion 112F.

When installed on the infusion device 100, the needle cover 114F with the pull tab portion 608 provides a small profile, and thus allows for a small envelope for packaging the infusion device 100. Additionally, during assembly, the configuration of the needle cover 114F may reduce side stresses to the needle cover 114F that may contribute to compromising a seal between the needle-covering portion 112F and the needle manifold.

To remove the combined release liner 500 and needle cover 114F from the infusion device 100, the patient the patient grasps and pulls the pull tab portion 608. Because the release liner 500 is retained between the pull tab hooks 612 and the flange 520F, such a single action removes both the release liner 500 and the needle cover 114F from the infusion device 100. Subsequently, the combined release liner 500 and the needle cover 114F are ready for disposal.

Figure 25A:
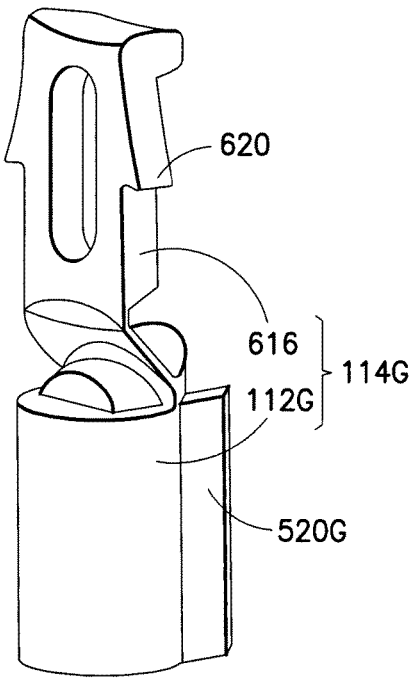
FIGS. 25A and 25B illustrate an embodiment of a needle cover in the infusion device of FIG. 1.
Figure 25B:
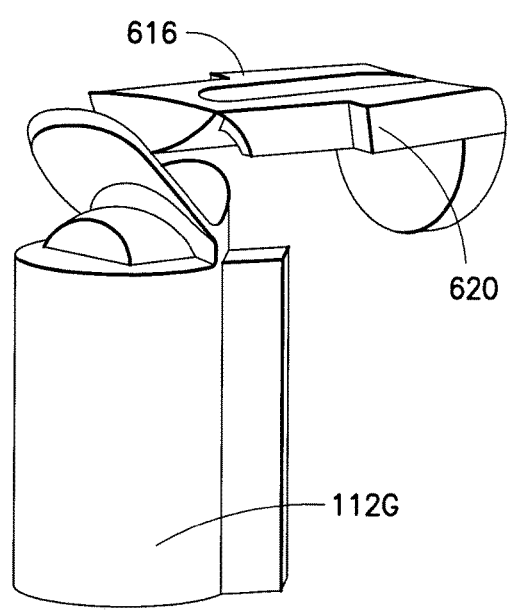

FIGS. 25A and 25B illustrate another embodiment of a needle cover 114G that is combinable with the release liner 500. As shown in FIGS. 25A and 25B, the needle cover 114G includes a needle-covering portion 112G and a pull tab portion 616, which includes a pair of pull tab hooks 620. At least one of the release liner 500 and the pair of pull tab hooks 620 is sufficiently elastically deformable that the pull tab hooks 612 are insertable through the liner opening 508. Subsequent to such an insertion, the release liner 500 is retained on the needle cover 114G between a flange 520G of the needle-covering portion 112G and the pull tab hooks 620.

According to one embodiment, the needle cover 114G is integrally formed as a unitary structure, and the pull tab portion 588 is connected to the needle-covering portion 112G by a living hinge, which is incorporated into a bi-stable hinge. A bi-stable hinge, such as can be found, for example, on shampoo or cosmetic bottle lids, remains stable in two positions. For example, the two stable positions of the needle cover 114G are a first position (FIG. 25A) substantially aligned with a main or longitudinal axis of the needle-covering portion 112G and a second position (FIG. 25B) approximately 90° from the first position. In the bi-stable hinge of the needle cover 114G, a thin web of material acts like a spring to bias the pull tab portion 616 toward both the first and second positions. For example, during rotation from the first position toward the second position, the bi-stable hinge biases the pull tab portion 616 toward the first position until a tipping point is reached, at which point the bi-stable hinge biases the pull tab portion 616 toward the second position.

When installed on the infusion device 100, the pull tab portion 616 of the needle cover 114G being configured in the second position provides a small profile, and thus allows for a small envelope for packaging the infusion device 100. Additionally, during assembly, the configuration of the needle cover 114G in the second position may reduce side stresses to the needle cover 114G that may contribute to compromising a seal between the needle-covering portion 112G and the needle manifold.

To remove the combined release liner 500 and needle cover 114G from the infusion device 100, the patient first rotates the pull tab portion 616 from the second position to the first position such that the pull tab portion 616 is substantially aligned with the needle-covering portion 112G. Then, the patient grasps and pulls the pull tab portion 616. Because the release liner 500 is retained between the pull tab hooks 620 and the flange 520G such a single action removes both the release liner 500 and the needle cover 114G from the infusion device 100. Subsequently, the combined release liner 500 and the needle cover 114G are ready for disposal.

According to one embodiment, the needle cover 114 (for example, the needle cover 114D, 114E, 114F, or 114G) is injection-molded as a single component, for example of thermoplastic elastomer (TPE). According to another embodiment, the needle cover 114 (for example, the needle cover 114D, 114E, 114F, or 114G) is injection molded in a two-shot process. For example, the pull tab portion 580 of needle cover 114D may be molded out of polypropylene and the needle-covering portion 112D of needle cover 114D may be molded of TPE is to possess a flexibility or elastic deformability to accommodate a press fit with the needle manifold.

Additionally, according to one embodiment, when the needle cover 114 is installed on the infusion device 100, for example, press fit with the needle manifold, the needle cover 114 interlocks with the rotor 136 to prevent rotation of the rotor 136 prior to removal of the needle cover 114.

As noted above, both the needle cover 114 and the release liner (e.g., 500) are removed prior to use of the infusion device 100. Accordingly, these removal actions can be integrated into a single action by employing the described embodiments, thereby increasing patient convenience, ease of use, and efficiency. Additionally, by optionally maintaining a connection between the needle cover 114 and the release liner subsequent to removal from the infusion device 100, the described embodiments can further increase patient convenience, ease of use, and efficiency by simplifying the disposal thereof.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

What is claimed is:

1. A drug delivery device, comprising:
   a body having a reservoir disposed therein for containing a medicament;
   an activator button operably connected with the body;
   an injection needle displaceable relative to the reservoir and adapted to penetrate the skin of a patient after the body is placed on the skin of the patient and the device is activated, the needle providing a path for the medicament between the reservoir and the patient; and
   a removable needle cover having:
      a first portion for covering the injection needle; and
      a second portion for preventing device activation prior to the body being placed on the patient's skin, the first and second portions being insertable through a same opening of the body;
   wherein the second portion extends directly from the first portion.

2. The device according to claim 1, wherein the second portion is adapted to prevent device activation until the first portion is removed to uncover the needle.

3. The device according to claim 1, wherein the second portion is engageable with an element disposed in the interior of the body to prevent activation.

4. The device according to claim 1, wherein the first and second portions are integrally formed as a unitary structure.

5. The device according to claim 1, wherein the needle cover comprises a handle portion rotatable relative to the first portion.

6. The device according to claim 1, further comprising an adhesive pad disposed on the body for contacting the patient's skin.

7. A drug delivery device, comprising:
   a body having a reservoir disposed therein for containing a medicament;
   a movable member movably disposed within the body;

an injection needle for penetrating the skin of a patient, the needle providing a path for the medicament between the reservoir and the patient; and a needle cover having a first portion for covering the injection needle and a second portion movable from a first position preventing device activation to a second position enabling device activation;

wherein the second portion extends directly from the first portion;

wherein in the first position, the second portion engages the movable member;

wherein the needle cover is removable from the body to enable device actuation; and wherein the first and second portions are insertable into a same opening in the body.

8. The device according to claim 7, wherein the first and second portions are integrally formed as a unitary structure.

9. The device according to claim 7, further comprising an adhesive pad disposed on the body for contacting a patient's skin.

10. A drug delivery device, comprising:

a body having a reservoir disposed therein for containing a medicament;

an injection needle displaceable relative to the reservoir and adapted to penetrate the skin of a patient after placement of the body on a patient's skin, the needle providing a path for the medicament between the reservoir and the patient, and having a longitudinal axis that is not parallel to a longitudinal axis of the reservoir; and a needle cover having:

a first portion for covering the injection needle; and a second portion for preventing device activation prior to placement of the body on the patient's skin;

wherein the second portion extends directly from the first portion.

11. The device according to claim 10, wherein the first and second portions of the needle cover are insertable through a same opening of the body.

\* \* \* \* \*